United States Patent [19]

Kimura et al.

[11] 4,319,270
[45] Mar. 9, 1982

[54] SURFACE INSPECTION SYSTEM FOR HOT RADIANT MATERIAL

[75] Inventors: Nobuo Kimura, Kobe; Yasuhide Nakai, Amagasaki; Yoshiro Nishimoto, Higashiosaka, all of Japan

[73] Assignee: Kobe Steel, Ltd., Kobe, Japan

[21] Appl. No.: 110,616

[22] Filed: Jan. 9, 1980

[30] Foreign Application Priority Data

Jan. 12, 1979 [JP] Japan .................. 54-00233[U]
Jan. 12, 1979 [JP] Japan .................. 54-002484
Jan. 12, 1979 [JP] Japan .................. 54-002485
Aug. 30, 1979 [JP] Japan .................. 54-111982

[51] Int. Cl.$^3$ .......................................... H04N 7/18
[52] U.S. Cl. ............................. 358/106; 358/93; 358/100; 358/101; 356/385; 250/560; 250/578
[58] Field of Search .............. 358/106, 93; 380/100, 380/101; 250/239, 560, 578; 356/384, 385

[56] References Cited

U.S. PATENT DOCUMENTS

| | | | |
|---|---|---|---|
| 3,049,588 | 8/1962 | Barmett | 358/106 |
| 4,131,490 | 12/1978 | Oishi et al. | 358/106 |
| 4,219,844 | 8/1980 | Ohsumi et al. | 358/106 |
| 4,223,346 | 9/1980 | Neiheisel et al. | 358/106 |
| 4,240,110 | 12/1980 | Henry | 358/106 |

*Primary Examiner*—Robert L. Richardson
*Assistant Examiner*—Edward L. Coles
*Attorney, Agent, or Firm*—Oblon, Fisher, Spivak, McClelland & Maier

[57] ABSTRACT

A surface inspection system detects imperfections on the surface of a hot radiant material, in which video signals for imperfections or defects are discriminated by comparison with normal level signals which are obtained through a variable area peak hold to preclude completely the influences of dark or bright defects which happen to be on the inspecting surface. The system includes apparatus for removing noises due to scales to produce outputs indicating true surface imperfections alone or indicating the degree of defectiveness of the detected defects. Also disclosed is a multi-camera surface inspection system capable of detecting defects on all sides of a hot radiant material which is transferred along a predetermined transfer line, with or without follow-up control of a camera or cameras scanning a given side of the material using edge signals detected from the normal level signal of another camera scanning a surface on the ensuing side of the material.

5 Claims, 45 Drawing Figures

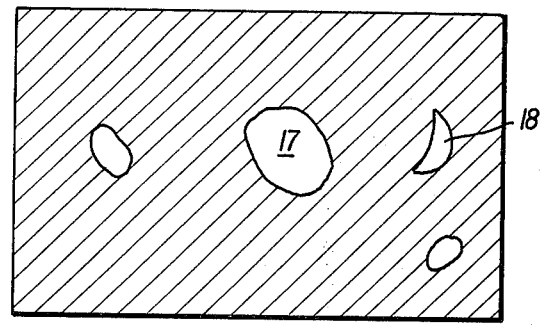
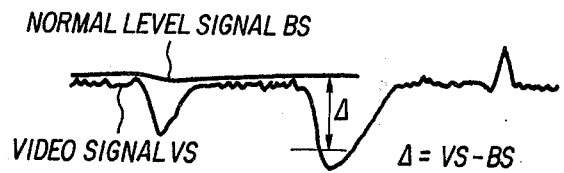
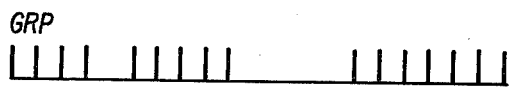
FIG. 2A
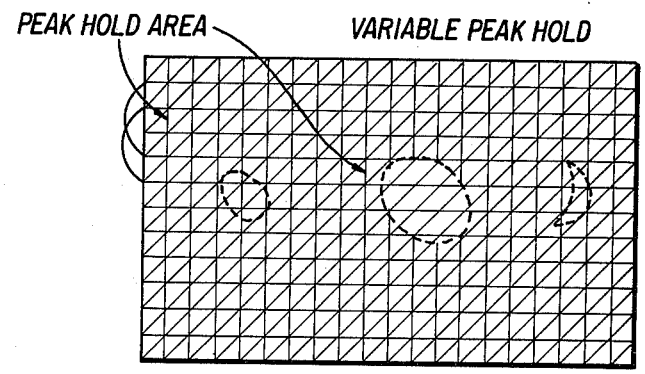
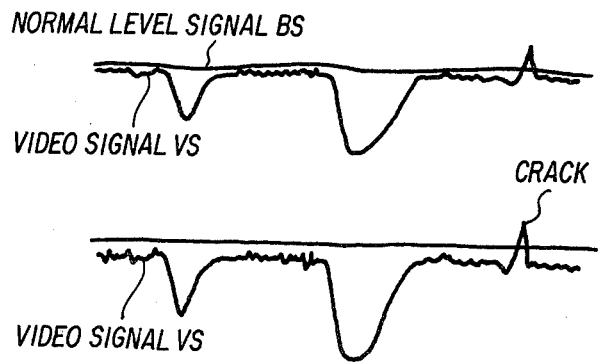
FIG. 2B

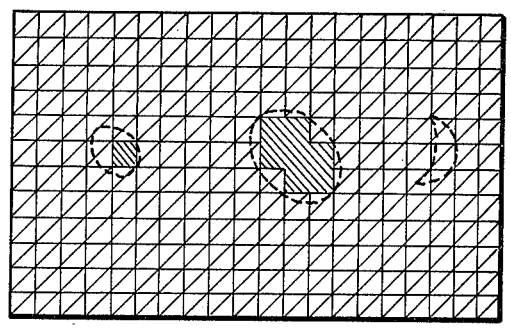
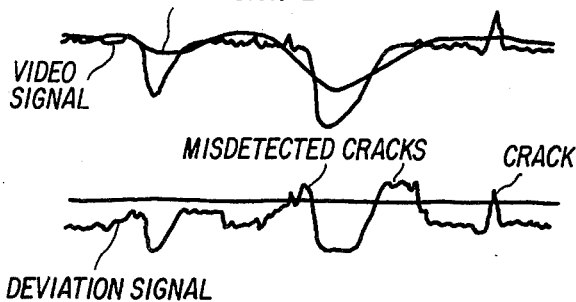
FIG. 3
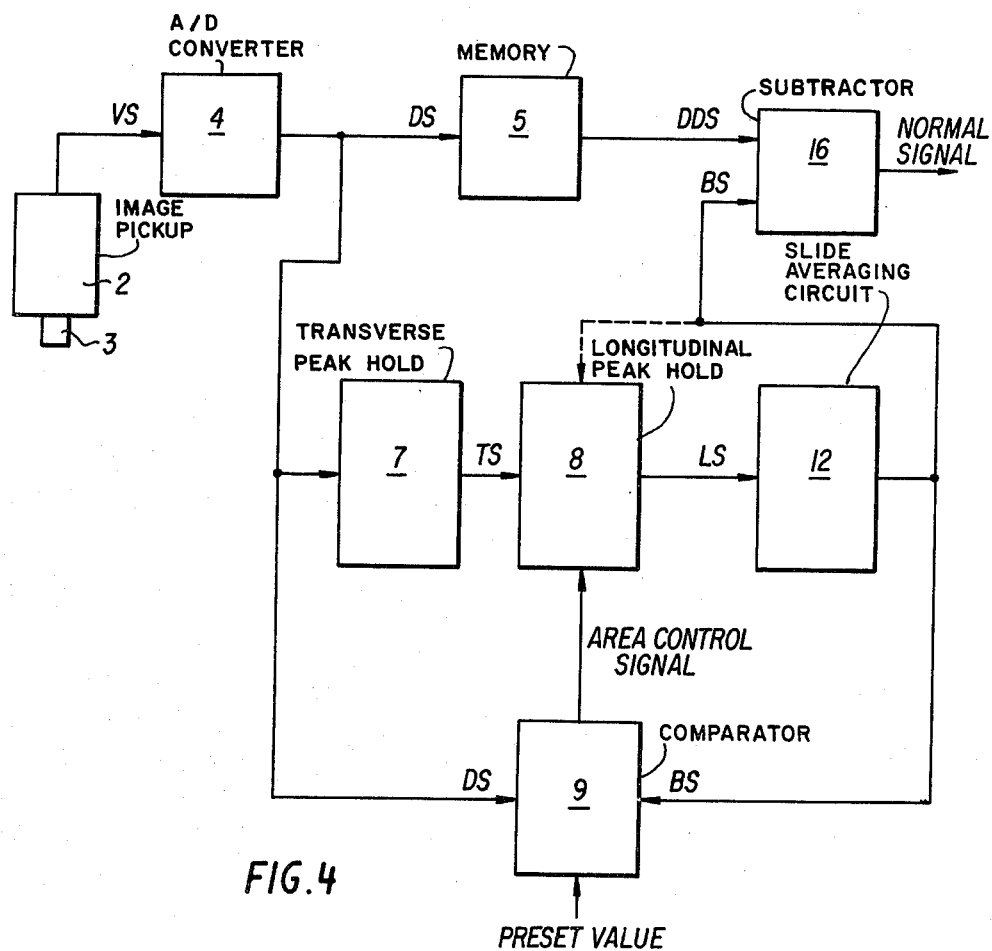
FIG. 4

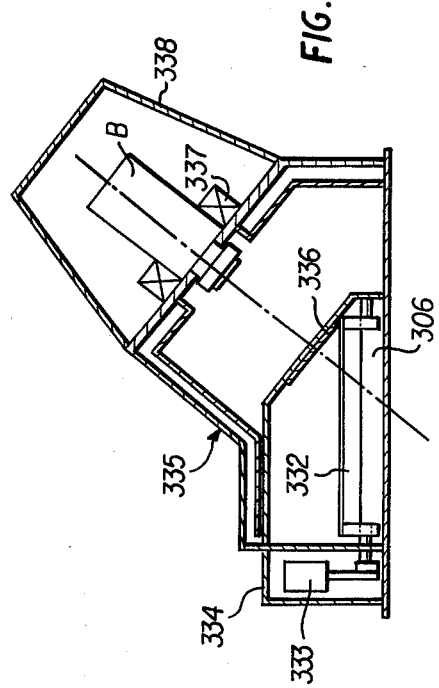
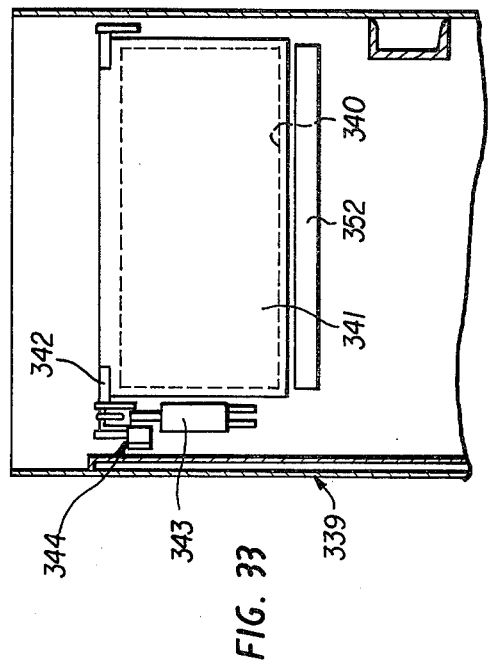
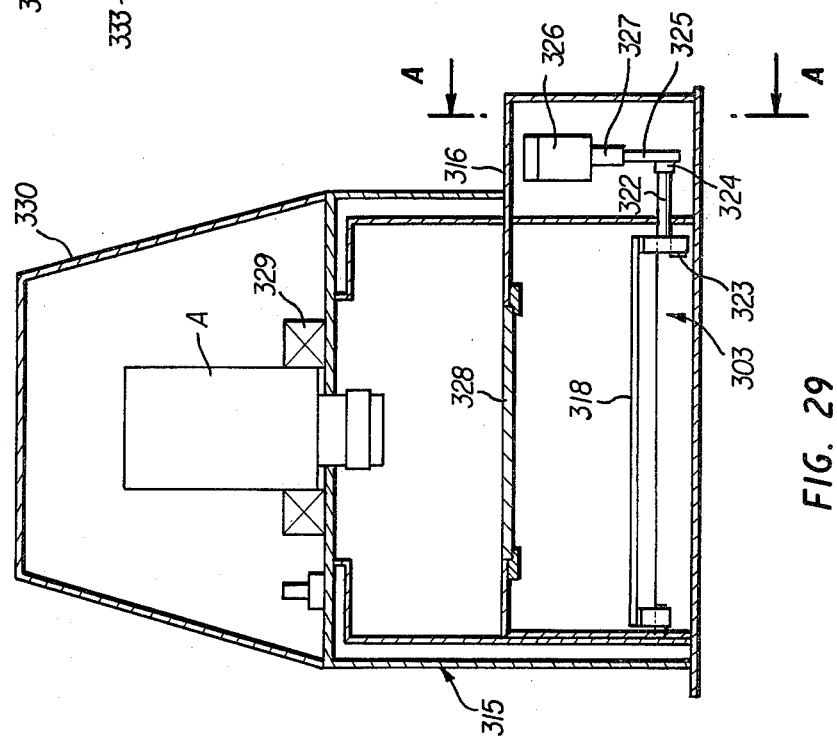

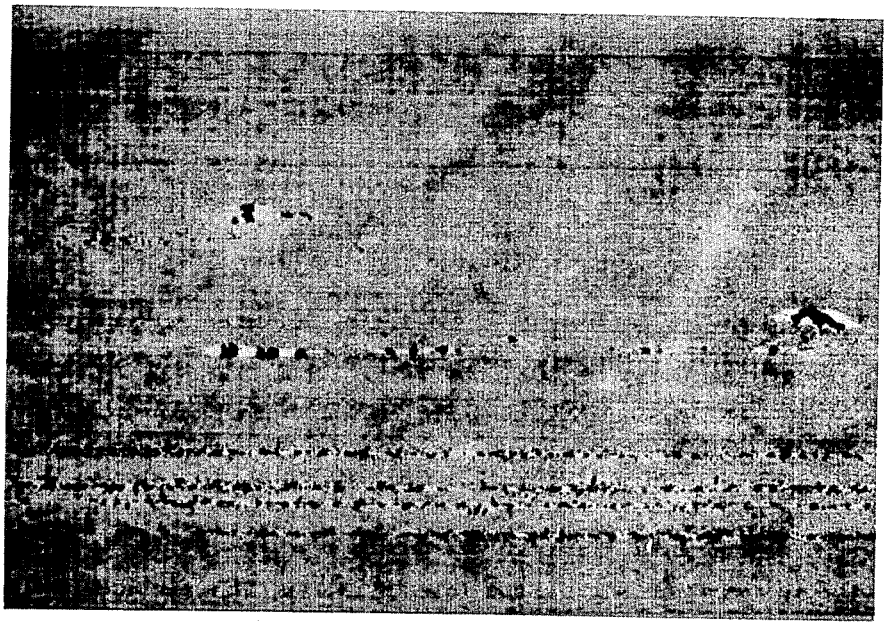
FIG. 41 DEVIATION IMAGE BASED ON CONVENTIONAL NORMAL LEVEL SIGNAL
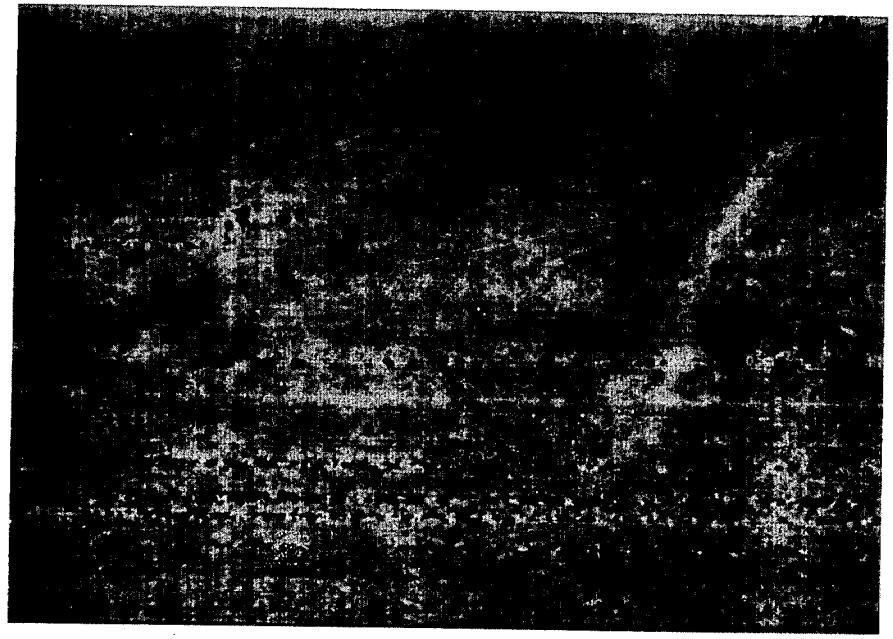
FIG. 42 DEVIATION IMAGE BASED ON NORMAL LEVEL SIGNAL OF INVENTION

SURFACE INSPECTION SYSTEM FOR HOT RADIANT MATERIAL

BACKGROUND OF THE INVENTION

This invention relates to a surface inspection system for detecting defects or imperfections on a surface or surfaces of a hot irradiant material.

Hot direct rolling has recently been widely employed in cogging operations as one of the measures for saving energy. As a result, there is an increasing demand in the art for techniques for detecting objectionable defects on the surface of a hot workpiece, to take the place of the conventional surface flaw detection at room temperature. If it is possible to provide means for detecting defects on the surface of a red hot steel slab which comes out of a cogging mill, the results can be applied for the adjustment of the amount of hot scarfing, hot spot scarfing, classification of quality and feedback to a preceeding process and contribute to the improvement of yield and quality as well as to the economy of manpower and energy. In this connection, there have already been proposed a number of techniques which claim thorough detection of defects on the surface of a hot steel slab on the basis of discernable differences in the amount of irradiant light from the surface being inspected.

Generally, as a hot steel slab of about 1000° C. is evenly cooled in the atmosphere, heat transmission occurs differently depending upon the surface and near surface conditions of the workpiece, showing a different surface temperature at those portions which bear defects or scales as compared with that of the normal or sound portions. More particularly, cracks which show the hotter inside of the material appear brighter while scabs, scales, deposits or other deflects with loose portions which cool off quickly due to low heat transmission appear darker than the remainder.

In most cases, the temperature distribution on the surface of a red hot steel material is not uniform. The surface temperature is lower in the corner portions than in the middle portions of the slab and the unevenness in the surface temperature is also produced by various factors, for example, by the differences in the amount of water which is poured on the slab during the rolling operation. Therefore, it is difficult to distinguish the temperature differences which are attributable to defects from temperature irregularities inherent in the hot steel slab simply by comparing them with a predetermined level.

For automatic detection of defects on the surface of a hot steel slab, the difference in temperature (brightness) of a defective portion from a sound portion has to be detected. Even in the case of eye observation, whether a particular point is defective or not is judged by comparison with the appearance of the circumventive areas. Therefore, it becomes necessary to remove from the detected data the components of the temperature pattern of a normal surface (normal level). The term "normal level" as herein used means the distribution of surface temperature inherent to a hot steel slab free of any surface defects, scales, deposits and the like.

The signals on one scan line are not always at a constant level not only in the inspection at high temperature but also in optical inspection so that it is difficult to detect defect signals by comparison with a predetermined normal level. In order to solve this problem, there have been proposed various methods for producing normal level signals on the basis of input video signals. However, it has been found that the normal level signals produced by the conventional methods are more or less influenced or biased by large dark or bright defects and fail to serve as a rule for measuring the input video signals.

In the scanner type automatic surface inspection of hot steel slabs as mentioned above, the surface of the workpiece which is divided longitudinally and transversely into a multitude of picture elements is scanned by a camera and resulting video signals indicative of the radiation intensity of the respective picture elements are successively processed to extract defect signals which are higher or lower than a normal level. However, as mentioned hereinbefore, the hot steel slabs usually bear, along with real defects, a large number of scales and uneven temperature spots which have radiation intensities confusingly similar to those of the real defects.

In the actual hot rolling operation, it is necessary to inspect for defects not only on the top surface but also on the side and bottom surfaces of the material without allowing any dead zones. However, the current surface inspection systems employ experimentally only one or a few number of overhead cameras due to the difficulties of controlling a number of cameras to maintain the inspecting surfaces within the focusing depths of the respective cameras on all sides of the conveyed material which often makes meandering movements and which considerably differs from one workpiece to another in width and travel position, while protecting the optical and electronic components against the heat radiation of the material and against defilement by scales or deposits which drop from the surfaces of the material.

SUMMARY OF THE INVENTION

It is an object of the present invention to provide a surface inspection system capable of detecting imperfections on the surface of a hot radiant material.

It is another object of the present invention to provide a surface inspection system of the class mentioned above, employing variable area peak hold to exempt normal level signals from the influences of dark or bright defects.

It is still another object of the present invention to provide a surface inspection system of the class mentioned above, employing dual-area analysis of the picture element data to separate noises of scale signals from defect signals.

It is a further object of the present invention to provide a surface inspection system of the class mentioned above, in which defect signals are discriminated by a discriminant curve employing the depth and width of the defect signals as parameters.

It is still another object of the present invention to provide a multi-camera surface inspection system capable of simultaneously inspecting all sides of a hot irradiant material which is transferred along a predetermined transfer line.

It is a further object of the present invention to provide a multi-camera surface inspection system of the type mentioned above, which is provided with means for controlling a camera or cameras scanning one side of the material to follow digressive movements of the material, the control being effected by edge signals detected from a normal level signal of a camera scanning a surface on the ensuing side of the material.

According to one aspect of the present invention, there is provided a method for detecting imperfections on the surface of a hot irradiant material, comprising the steps of: obtaining a video signal by electro-optically scanning a radiant light image of the hot material; feeding the video signal to a memory for delay over a predetermined time interval and at the same time feeding the video signal to a peak hold circuit for holding peak values of the video signal as divided in the scanning direction into a number of picture elements by picture splitting pulses; upon obtaining for each picture element a normal level signal by sequentially averaging peak values of a number of picture elements in adjoining areas, comparing the video signal or a peak signal as obtained by passing the video signal through the peak hold circuit with a current normal level signal obtained in a previous operation, slide-averaging fractional signals of said video or peak signals wherein a fractional signal having a difference from said current normal level signal in excess of a preset value is gated and instead previously obtained fractional signal is used for the slide-averaging; and comparing the delayed video signal from the memory with the next normal level signal and discriminating a surface imperfection according to the difference between the delayed video signal and a normal level signal.

More particularly, the present invention obtains the normal pattern signals corresponding to the inherent surface temperature pattern of the workpiece by the following two steps of operations (I) and (II).

(I) In order to remove the influences of the defects and scale which might exist on the surface of the workpiece, the video signal is fed to a peak hold circuit of variable area for automatically varying the area of peak detection according to the size of the defect or scale. The normal pattern signal and a fresh input signal are compared and if their difference is greater than a predetermined value, the peak hold area is widened to detect a peak value free of influences of a dark portion due to a scab, scale, deposit or the like.

(II) The peak values obtained in (I) are slide-averaged. The normal pattern signal should be smooth enough by nature so that the slide averaging is effected over a certain area in consideration of the spatial frequency of the temperature distribution on the material surface.

According to another aspect of the present invention, the surface inspecting method further comprises: longitudinally and transversely dividing the surface of the material into a multitude of picture elements and collecting particular picture element data by comparing the video signal or peak signal for each picture element with a normal level signal; preliminarily analysing the surface by shifting sequentially from one picture element to another a small area covering a predetermined number of picture elements in rows and columns while comparing in each shifted position the number of the picture element data in the small area with the total number of picture elements thereof; and then analysing the surface by shifting sequentially from one picture element to another a large area covering a predetermined number of picture elements in rows and columns while comparing in each shifted position the number of the picture element data in the large area with the total number of picture elements thereof.

According to still another aspect of the present invention, the method further comprises: extracting subsiding portions of said video signal which fall beneath a preset normal level $P_o$; obtaining the depth P and width W of each subsiding signal portion; calculating a value of a discriminant equation $$f(P, W) = \frac{W}{\alpha + \{\beta(P - P_o)\}\gamma}$$

by inserting said depth P and said width W to said discriminant equation to thereby discriminate the degree of defectiveness on the surface of a hot radiant material in which a defect data map for various combinations of parameters (P,W) is prepared by analysing video signals of at least one similar hot material in relation with actual surface conditions and parameters $\alpha, \beta$ and $\gamma$ of said discriminant equation are so pre-experimentally determined by the use of said defect data map as to give a judgement of "defect" when f(P,W) is equal to or greater than a preset value and a negative judgement when f(P,W) is less than said preset value.

According to a further aspect of the present invention, there is provided a surface inspection system for simultaneously inspecting by a plural number of line scan cameras the top, bottom and side surfaces of a hot irradiant material which is travelling over a predetermined transfer passage, the line scan cameras being positioned to scan along lines of intersection where the respective surfaces of the material are intersected by a plane which is disposed perpendicular to the travel direction of the material, comprising: a top line scan camera positioned overhead of the transfer passage to scan in the perpendicularly intersecting plane a line of intersection on the top surface; a pair of side line scan cameras positioned overhead of the transfer passage and on the outer sides of the top line scan camera to scan in the perpendicularly intersecting plane the opposite end portions of the line of intersection on the top surface and lines of intersection on opposite side surfaces of the material, the side line scan cameras having a focusing depth of field greater than the thickness of the material and a tilted alignment of the optical components; and a pair of lower line scan cameras positioned beneath and on the opposite sides of the transfer passage to scan obliquely from beneath a line of intersection on the bottom surface of the material in a plane containing the line of intersection on the bottom surface and slanted downward in the travel direction of the material, the lower line scan cameras having a tilted alignment of their optical components.

According to a further aspect of the present invention, there is provided a camera follow-up control device for a surface inspection system of the type which employs more than one camera for simultaneously viewing different surfaces of a hot irradiant material in travel over a transfer passage and which is provided with means for processing video signals into normal level signals thereby to discriminate imperfections on the material surfaces, the follow-up control device comprising: means for detecting edge signals by comparing the normal level signal of one of two adjacent surfaces with a preset value; and means for controlling follow-up movements of a camera for the other one of the two adjacent surfaces in accordance with the detected edge signals.

BRIEF DESCRIPTION OF THE DRAWINGS

The above and other objects, features and advantages of the present invention will be apparent from the following particular description and appended claims, taken in conjunction with the accompanying drawings which show by way of example preferred embodiment of the invention and in which:

FIGS. 2 A & B are diagrammatic views explanatory of the operations of the variable peak hold;

FIG. 3 is a diagrammatic view explanatory of the operations by a conventional counterpart;

FIGS. 4 and 5 are block diagrams showing modified arrangements for the variable area peak hold;

FIG. 29 is a diagrammatic sectional view of a top line scan camera and its shutter;

FIG. 31 is a diagrammatic sectional view of a side line scan camera and its shutter;

FIG. 33 is a diagrammatic back view of the shutter of FIG. 32;

FIG. 41 is a photograph showing a deviation image of a hot steel slab based on a conventional normal level signal;

FIG. 42 is a photograph showing a deviation image of a hot steel slab based on a normal level signal according to the present invention;

DESCRIPTION OF PREFERRED EMBODIMENTS

Figure 1:
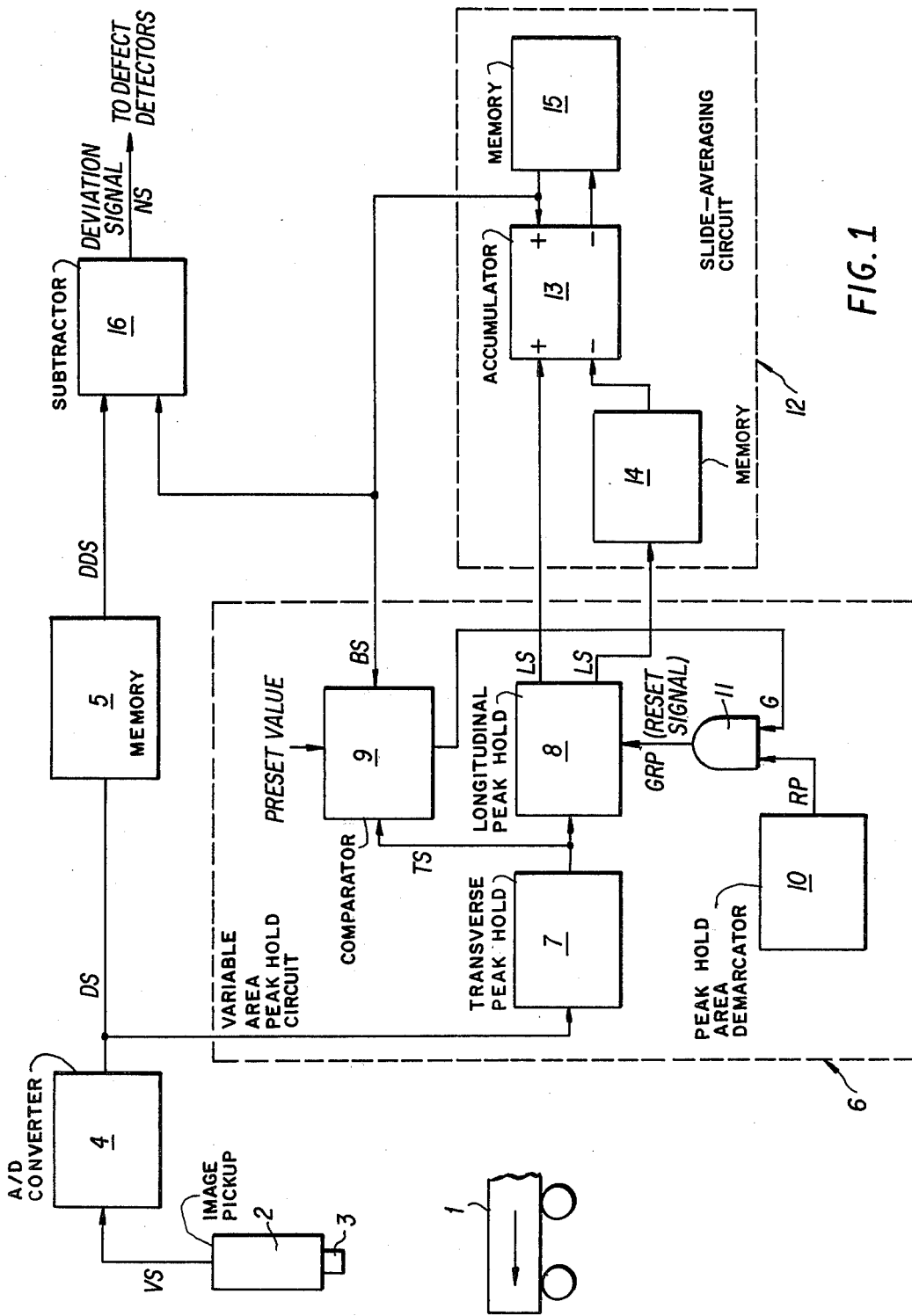
FIG. 1 is a block diagram of a variable area peak hold circuit according to the invention.

Referring to FIG. 1, a high temperature workpiece, in this case, a hot steel slab 1 is scanned by an image pickup device such as a TV camera or solid state image sensor which sweeps the surface of the workpiece in a direction perpendicular to the direction of travel of the steel slab 1 as indicated by the arrow on slab 1 in FIG. 1. The radiant light image of the slab 1 is picked up through an optical arrangement including a lens and a filter to produce a video signal VS. The video signal produced by the image pickup device 2 is converted by an A/D converter 4 into digital signals DS, for example, of 8 bits (256 steps) and fed to two separate lines, one of which is provided for performing the averaging operation. More particularly, the digital signals DS are fed on one hand to memory 5 for delaying the same for a predetermined time interval and on the other hand to a variable area peak hold circuit 6. In the variable area peak hold circuit 6, the digital signals DS enter a transverse peak hold circuit 7 which detects and holds the peak for each predetermined number of picture elements (e.g., $n_1=4$) in the transverse row (normally lying widthwise of the hot steel slab 1) thereby producing transverse peak hold signals TS. Each transverse peak hold signal TS is fed to a longitudinal peak hold circuit 8 and to a comparator 9 which compares the received transverse signal TS with a current normal level signal BS. If the difference of the transverse signal TS from the current normal level signal BS is greater than a predetermined value $\epsilon$ (approximately 1/10 to 1/40 of the dinamic range of the video signal), that is to say, if $$|BS|-|TS|>\epsilon \qquad (1)$$

(as in the case of the scanning point coming to a dark portion due to a scab, scale or deposit), the comparator 9 dispatches a gate signal G to a gate circuit 11 to gate a resetting pulse RP which is produced by a peak hold area demarcating generator 10 for each predetermined number of scanning lines (e.g., $n_2=4$). The longitudinal peak hold circuit 8 holds as a longitudinal peak hold signal LS the peak of signals of a plural number of longitudinally ensuing picture elements (lying in the longitudinal direction of the hot steel slab 1) until it is reset by a gated resetting pulse GRP. If the resetting pulse RP from the peak hold area demarcator 10 is gated at the gate circuit 11 by the gate signal G and blocked to be applied to the longitudinal peak hold circuit 8 as a reset pulse RS, the longitudinal peak hold is continued without renewing the area. This means that when the scanning point comes to a defective dark portion, the peak value immediately before the dark portion is held so as to ignore that defective dark portion. As soon as the scanning point comes out of the defective dark portion, the gate signal G disappears since the condition of formula (1) is not satisfied any longer, the reset pulse GRP being fed to the longitudinal peak hold circuit 8 at every $n_2$ scanning lines to return to a normal peak hold of a predetermined area.

The longitudinal peak hold signals LS, which are deprived of the dark portions in the above-described manner, are fed to a slide-averaging circuit 12. If the longitudinal peak hold signals LS which are fed in sequence to the input of the slide-averaging circuit 12 are designated as $LS_1$, $LS_2$ . . . $LS_{n1}$, an accumulator 13 starts to add them one after another for N bits from the time point when the current normal level signal is cleared, as follows, $$, N \times BS_n = LS_1 + LS_2 + \ldots + LS_n \qquad (2)$$

obtaining a new normal level signal $BS_n$ for the time point of t=N. As the accumulator 13 receives a new longitudinal peak signal $LS_{n+1}$ at its positive terminal, it simultaneously receives at its negative terminal the signal $LS_1$ which has been delayed by N bits through memory 14, giving the normal level signal $BS_{n+1}$ for the time point t=N+1 as follows.

$$N \times BS_{n+1} = LS_1 + LS_2 + .. LS_n + LS_{n+1} - LS_1 \qquad (3)$$
$$= LS_2 + LS_3 + \ldots + LS_{n+1}$$

In the same manner, the longitudinal peak signals LS from the longitudinal peak hold circuit 8 are slide-averaged one after another to give average values which sequentially serve as normal level signals $BS_{n\,2}$, $BS_{n\,3}$ and so forth. The normal level signals BS are stored in memory 15.

The normal level signal BS obtained by the variable area peak hold and slide-averaging is fed to a subtractor 16 along with the corresponding delayed digital signal DDS which has been delayed through the memory 5 for a predetermined time length for synchronization with the normal level signal BS. The subtractor 16 produces a deviation signal NS according to the difference of the delayed digital signal DDS from the normal level signal BS. Since the surface temperature irregularities inherent to the hot steel slab 1 have already been removed from the deviation signals NS, the defective portions can be securely detected by comparing them with a predetermined level. Thus, there can be obtained ideal normal level signals BS which are not influenced by the defects or scales which might exist on the surface of the hot steel slab 1.

FIGS. 2A and 2B diagrammatically illustrate the principles of the detection of the above-described normal level signals BS. In a case where the hot steel slab 1 has on its surface a scab 17 and a crack 18, video signal VS and normal level signal BS as shown in FIG. 2A are compared to block the reset pulse GRP to be fed to the longitudinal peak hold circuit 8 when the value deviation $\Delta$ exceeds $\epsilon$. Therefore, the area of peak hold is expanded in both forward and rearward directions as the scab 17 and the crack 18 can be detected easily and reliably by comparison with the normal level signal BS which is immune from the influence of the scab 17.

For the purpose of comparison, FIG. 3 illustrates the results of a conventional peak hold of fixed area in a similar case. As is clear from FIG. 3, the normal level signal resulting from the fixed area signal processing is adversely affected by the dark portion of the scab 17 so that false bright defects appear in the vicinity of the dark defect.

The adverse effect of the dark defect is also clear from FIG. 41 which shows a deviation image of a hot steel slab having a dark defect in the central and right end portions thereof, which was obtained on the basis of the conventional normal level signal (peak hold of fixed area). The image produces false information as if bright defects such as cracks exist in the vicinity of the scabs.

In the present invention, the area of peak hold is varied upon detection of a dark portion to obtain a deviation signal which is ideal for the detection of surface defects and which, when displayed as shown in FIG. 42, contains no false bright portions of the vicinity of dark portions or any other influences of the dark defects.

Figure 43:
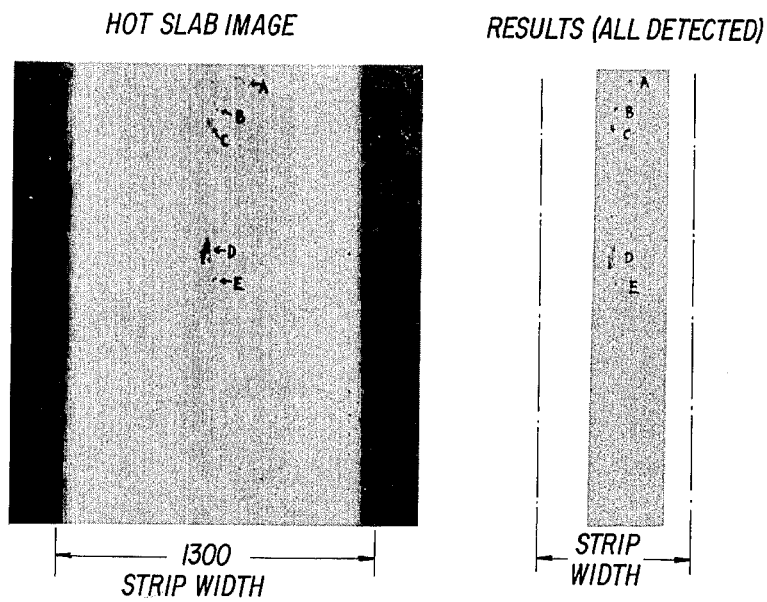
FIG. 43 is a photograph showing an example of detection.
Figure 44:
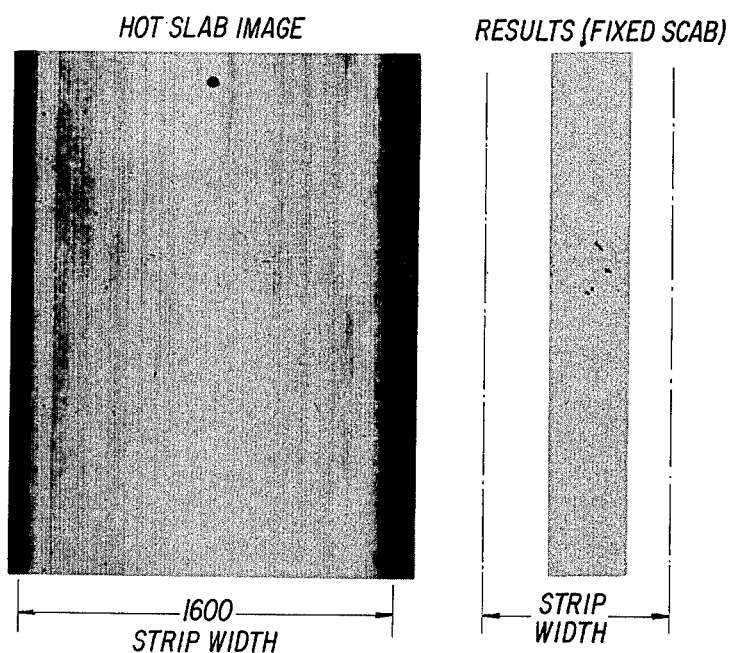
FIG. 44 is a photograph showing another example of detection.

Inspection of hot steel slabs by an automatic surface inspecting apparatus incorporating the present invention resulted in detection of defects with a high S/N ratio as shown in FIGS. 43 and 44, in which a radiant image of the hot slab is shown side-by-side at the left of the results of detection as obtained on a graphic printer. This high precision detection of the defects warrants the normal level signal according to the present invention.

In the foregoing description, a dark portion is recognized by comparing the transverse peak hold signal TS with the normal level signal BS. However, arrangements may be made to compare the digital signal DS with the normal level signal BS by a comparator 9 as shown in FIG. 4. Further, upon detection of a dark portion, the normal level signal BS may be fed to the transverse peak hold circuit as a signal which precedes the detected dark portion, as indicated by broken line, instead of the preceding peak hold signal (transverse or longitudinal).

Figure 5:
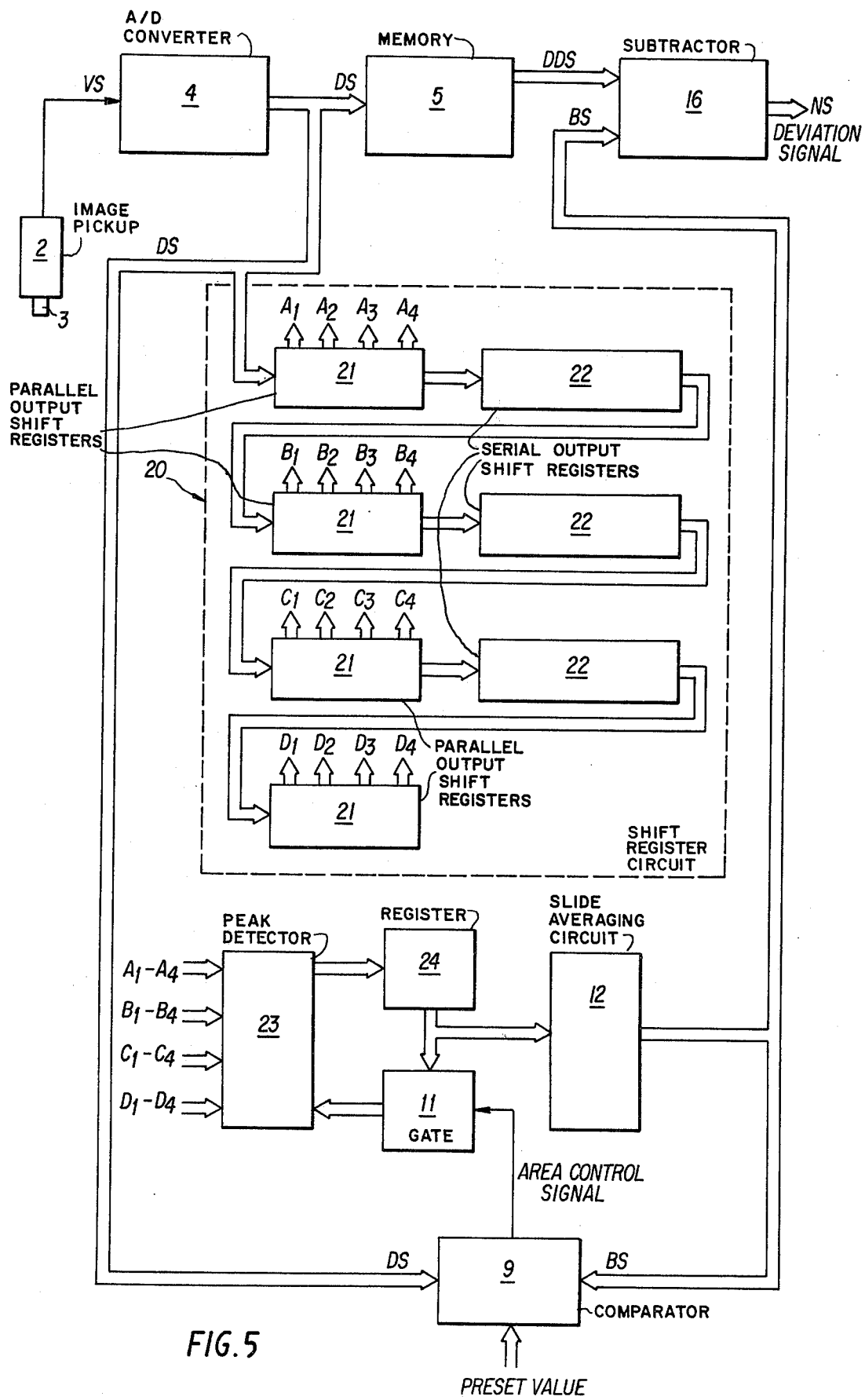

FIG. 5 shows in block diagram form a circuit arrangement in which the area of peak hold is normally fixed and, in the event of detection of a dark portion, a signal immediately preceding the dark portion is fed to the slide-averaging circuit. More particularly, the digital signal DS from the A/D converter 4 is fed to the memory 5 and to rows of shift registers 20, each row consisting of n-number of m-bit parallel output shift registers 21 and (n−1) number of serial output shift registers 22 (m=4 and n=4 in the example shown in FIG. 5). The m×n 8-bit digital signals at the outputs of the parallel output registers 21 are all fed to a peak detector 23 which detects the peak value among the m×n data and which detects, in the case which will be explained below the peak, value in the signal which is fed thereto from a register 24 through gate 11. The detected peak value output of the peak detector 23 is stored in the register 24. On the other hand, the comparator 9 compares the original digital signal DS with a current normal level signal BS. When the difference between the two signals is smaller than the predetermined value $\epsilon$, the comparator 9 produces no area control signal so that the gate 11 remains closed without referring to the peak of the preceding area. In other words, the peak is determined solely for the m×n area (fixed area peak hold). When the difference of the digital signal DS from the normal level signal BS is greater than the predetermined value $\epsilon$, the comparator 9 produces at its output an area control signal to open gate 11. As a result, the peak value of the preceding area which is stored in the register 24 is fed to the peak detector 23. This means that the area of peak hold is expanded upon receipt of a video signal which is materially greater than the normal level signal BS, thereby precluding the influences of dark defects.

In the embodiments of FIGS. 1, 4 and 5, the variable area peak hold is applied to remove the adverse effects of dark defects in the process for producing the normal level signal BS. However, it is to be understood that the variable area peak hold can be applied also for removing false drops in the normal level signal which may occur in the vicinity of bright defects such as cracks and depressions, similarly by comparing the video signal VS (or transverse peak hold signal TS) with the normal level signal BS and widening the area of peak hold when the difference between the two signals exceeds the predetermined value $\epsilon$. The resulting normal level signal BS is not biased by bright defects so that the precision of the flaw detection in the neighborhood of bright defects can be improved. Of course, it is possible to remove the adverse effects of both dark and bright defects by similar operations.

Figure 6:
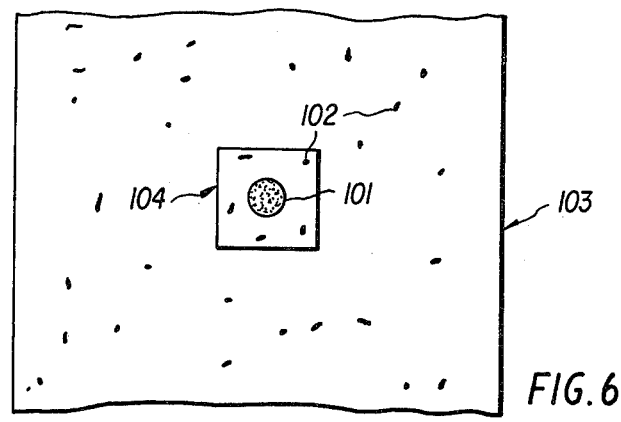
FIG. 6 is a diagrammatic view of a surface bearing imperfections.

Now, it is supposed that a large inspection area is spotted on a hot workpiece 103 which contains a scab 101 and a number of scales 102 on its surface as shown in FIG. 6. The large inspection area consists of a predetermined number of picture elements (16×16 picture elements) and contains a defect 101 and a number of scales 102 as indicated by hatching in FIG. 7. When the surface of the workpiece 103 is scanned, the video signals picked up from the hatched picture elements indicate temperature levels lower than the corresponding normal levels.

Figure 7:
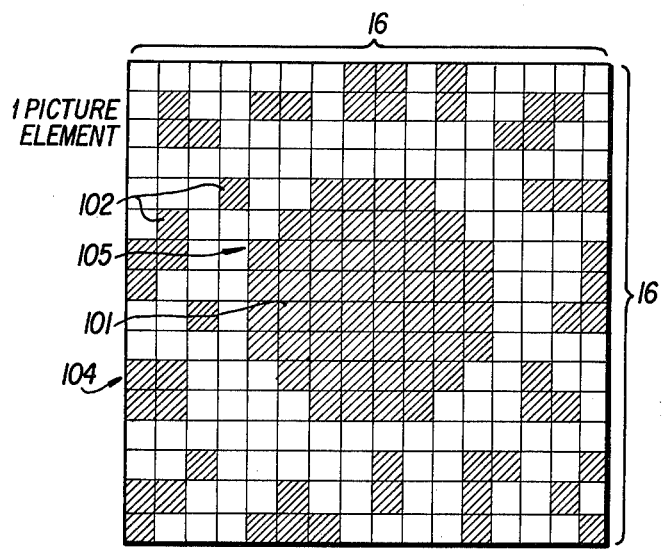
FIGS. 7 to 9 are diagrammatic views explanatory of dual area surface inspection.

According to the conventional detecting method, the surface condition is judged simply by counting the number of hatched picture elements within the inspection area 104, mistaking scales 102 for the same surface imperfection as the defect 101. In the example of FIG. 7, although the actual defect 101 has a size of 52 picture elements, the conventional method judges the inspection area 104 as containing defects over 104 picture elements, including 52 picture elements which are occupied by scales 102.

Figure 8:
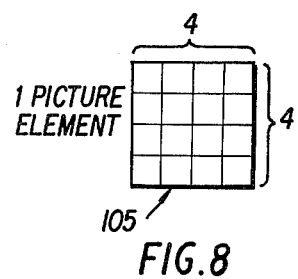
Figure 9:
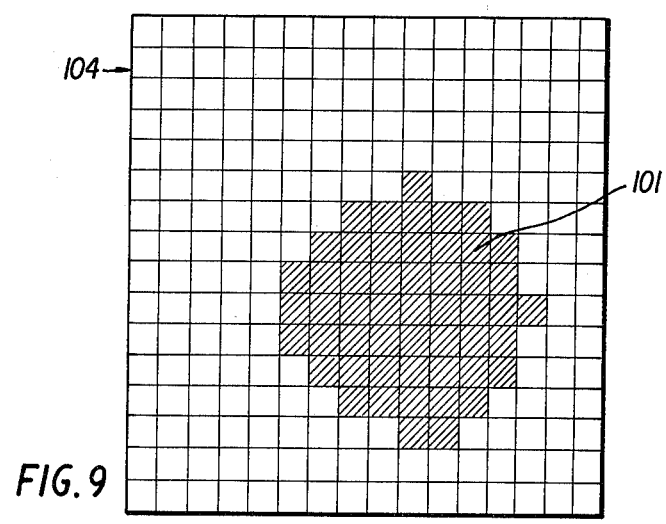

In the present invention, a small inspection area 105 (4×4 picture elements) as shown in FIG. 8 is shifted all over the inspection area 104, each time by one picture element, judging as defective those small areas which are occupied by hatched portions in a proportion greater than a predetermined value. Thereafter, the surface condition of the inspection area 104 is judged by counting the number of the defective portions. If the example of FIG. 7 is judged on the basis of the smaller areas 105, the inspection area 104 is found to have a single defect over 52 picture elements as shown in FIG. 9. The results thus indicate the size of the actual defect 101 irrespective of existence of the scales 102. In this case, the critical value for judging each small area 105 is 8. By inspecting the surface of the workpiece 103 in this manner, the defects 101 can be detected reliably and quickly without being misguided by the signals of the scales 102.

Figure 10:
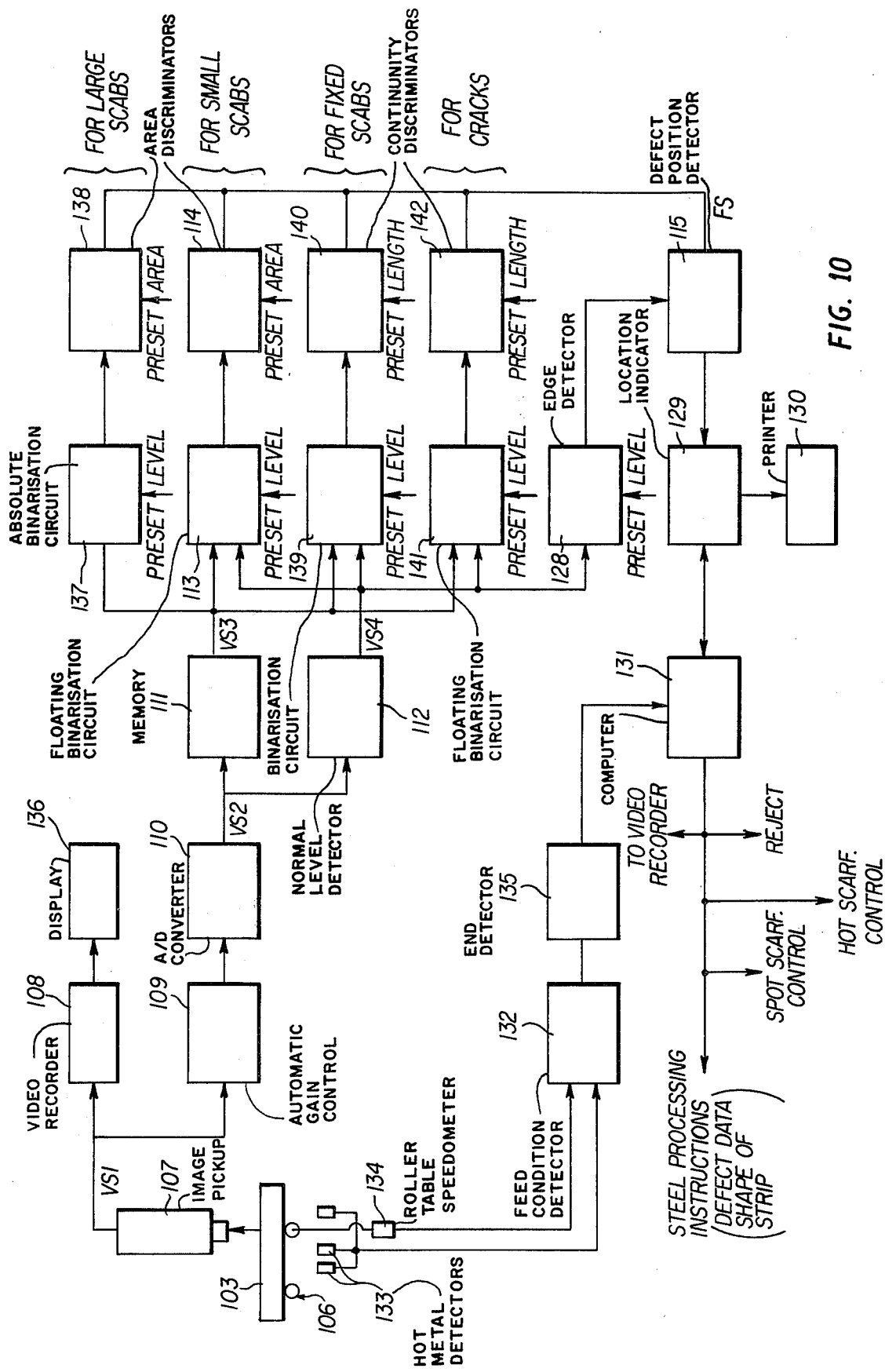
FIG. 10 is a block diagram of a dual area flaw detector.

FIG. 10 illustrates a signal processing system for performing the above-described operations. In FIG. 10, the radiant image of a workpiece 103 which is transferred on a roller table 106 is picked up by an image pickup device 107 which scans the workpiece 103 in a direction substantially perpendicular to the direction of travel of the workpiece 103 to produce video signal VS.

The video signal VS from the image pickup device 107 is recorded in a video recorder 108 and at the same time is fed to an A/D converter 110 through an automatic gain control 109 for conversion into a digital video signal $VS_2$. The automatic gain control 109 is provided for adjusting the detectability according to the temperature of the workpiece 103 being inspected. The digital video signal $VS_2$ is fed to memory 111 for delaying the same for a predetermined time interval (for several scanning lines). The digital signal $VS_2$ is also fed to a normal level detector 112 which produces a normal level signal $VS_4$ indicative of the temperature level which the surface of the workpiece 103 would have if there were no defects or scales, as described hereinbefore. Indicated at 113 is floating binarisation circuit of dark portion which includes a subtractor for determining the value between subtracting the normal level signal $VS_4$ from the normal level detector 112 from the delayed video signal $VS_3$ received from memory 111 and a comparator which produces at its output binary logic 1 when the value is less than a predetermined negative value. This output is fed to an area discriminant circuit 114 which calculates the defective area in the manner as described hereinbefore, producing a defect signal FS of a binary logic 1 when the defective area is larger than a predetermined value. The defect signal FS is fed to defect position detector 115. The above-mentioned floating binarisation circuit for dark portion 113 and discriminant circuit by area 114 are arranged as shown in FIG. 11.

Figure 11:
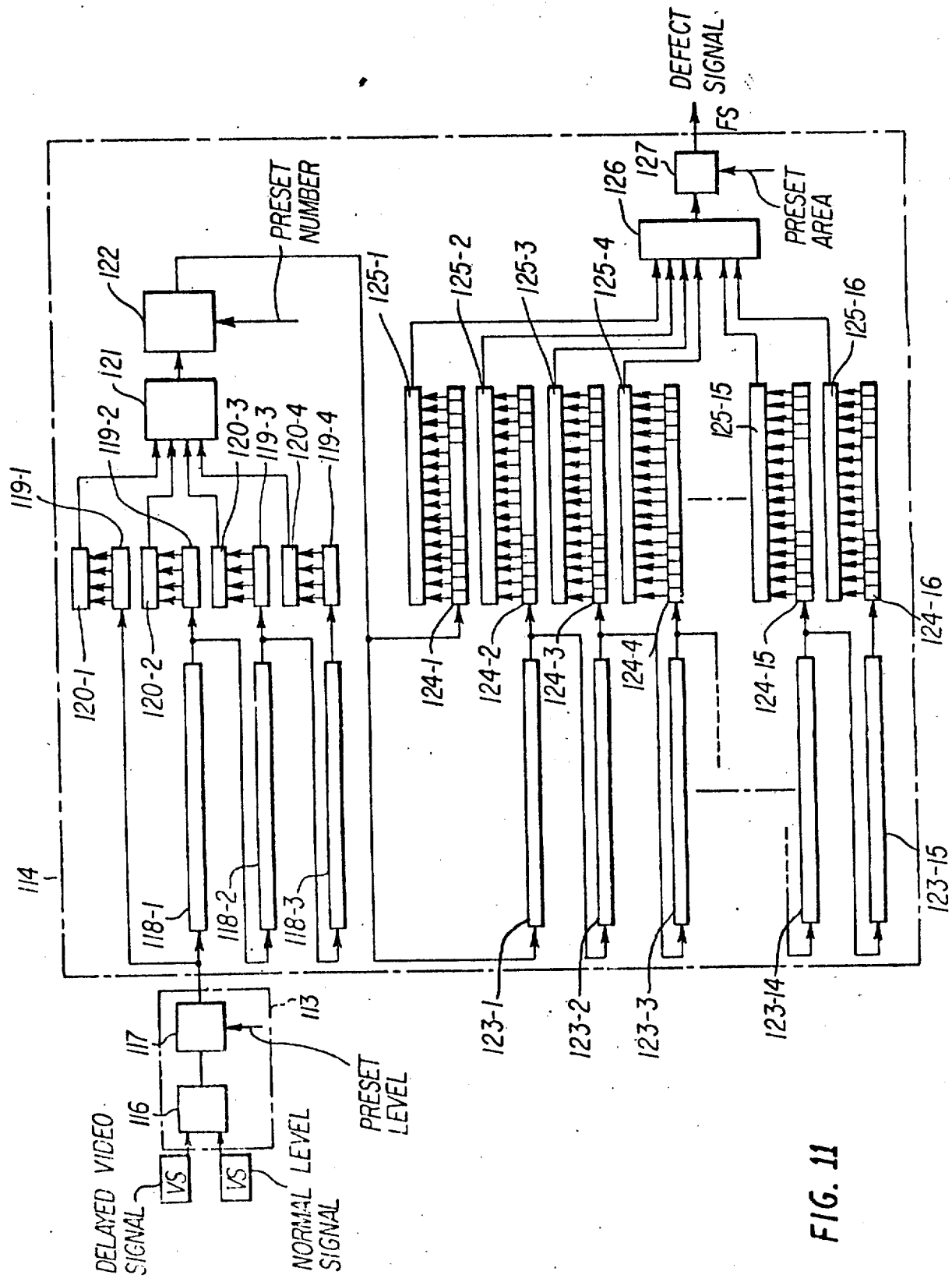
FIG. 11 is a block diagram of an area discriminator shown in FIG. 10.

In FIG. 11, designated at 116 is an 8-bit subtractor which produces at its output a signal indicative of the difference between the delayed video signal $VS_3$ and the normal level signal $VS_4$. The differential signal is compared with a predetermined value L by a comparator 117 which produces at its output a binary logic 1 when the difference is less than a predetermined value. The output of the comparator 117 is fed to 2048-bit shift registers 118-1 to 118-3 which delay the received signal for a time interval necessary for judging the small area 105. The signals indicative of the contents of the small area 105 (4×4 picture elements) are produced at the outputs of 4-bit parallel output shift registers 119-1 to 119-4, which are all read out and added by adders 120-1 to 120-4 and 121. The result is compared with a preset number N by a comparator 122 which produces at its output a binary logic 1 when the result is greater than the preset number N. The output of the comparator 122 is fed to 2048-bit shift registers 123-1 to 123-15 which delay the signal for a time interval necessary for judging the large area 104. The signals indicative of the contents of the large area 104 are produced at the outputs of 16-bit parallel output shift registers 124-1 to 124-15, which are all read out and added by adders 125-1 to 125-16 and 126. The result is compared with a preset value S by a 16-bit comparator 127 which produces at its output a defect signal of a binary logic 1 when the result is greater than the preset value S.

Reverting to FIG. 10, designated at 128 is an edge detector which compares the normal level signal $VS_4$ from the normal level detector 112 with a predetermined value by a comparator to detect the edges of the workpiece where the signal becomes higher or lower than a predetermined level. Defect locator 115 calculates the location of the defect on the basis of the edge signal from the stock edge detector 128 and the above-mentioned defect signal FS. The result is displayed on a printer 130 through a location indicator 129 and at the same time fed to computer 131. A feed condition detector 132 detects the presence or absence and the travel speed of the workpiece 103 from the signls received from a hot metal detector 133 and a roller table speedometer 134. An end detector 135 detects the leading and rear ends of the workpiece from the signal received from feed condition detector 132, transmitting its output signals to computer 131. If necessary, computer 131 controls the video recorder to show (play back) the condition of the defects on a display device 136 based on the signals thus received. Computer 131 calculates the defective area and makes higher decisions on the surface quality in consideration of positions of detected defects. The results are used for the decision of rejection, hot scarf control, spot scarf control, and steel processing instructions (information on defects, shapes of material etc.). The reference numeral 137 denotes an absolute binarisation circuit of dark portions which compares the delayed video signal $VS_3$ from memory 111 with a predetermined value and produces at its output a binary logic 1 when the delayed video signal $VS_3$ is less than the predetermined value. The output of the binarisation circuit 137 is fed to an area discriminator 138 which calculates the defective area by the method described hereinbefore, producing at its output a defect signal of a binary logic 1 when the calculated defective area is greater than a preset value. A binarisation circuit for signal width and height 139 determines the difference between the delayed video signal $VS_3$ received from memory 111 and the normal level signal $VS_4$ from the normal level detector 112 and discriminates a defect signal by making calculations using the width and height of the differential signal as parameters. The output of the binarisation circuit 139 is fed to a continuity discriminator 140 which calculates the length of a defect based on the continuity of defective signals and produces at its output a defect signal of a binary logic 1 when the detected length is greater than a predetermined value. Indicated at 141 is a floating binarisation circuit which determines the difference between the delayed video signal $VS_3$ received from memory 111 and the normal level signal $VS_4$ from normal level detector 112 by a subtractor and compares the resulting differential signal with a predetermined value by a comparator, producing at its output a binary logic 1 when the differential signal is greater than the predetermined value. This output is fed to a continuity discriminator 142 which calculates the length of a defect on the basis of the continuity of received defect signals and produces at its output a binary logic 1 when the detected length is greater than a predetermined value.

In the foregoing inspection system, small scabs are detected by the floating binarisation circuit for dark portion 113 and the area discriminator 114, large scabs are detected by the absolute binarisation circuit for dark portion 137 and the area discriminator 138, fixed scabs are detected by the binarisation circuit for signal width and the height 139 and continuity discriminator 140, and cracks are detected by the floating binarisation circuit for bright portion 141 and the continuity discriminator 142.

Figure 12:
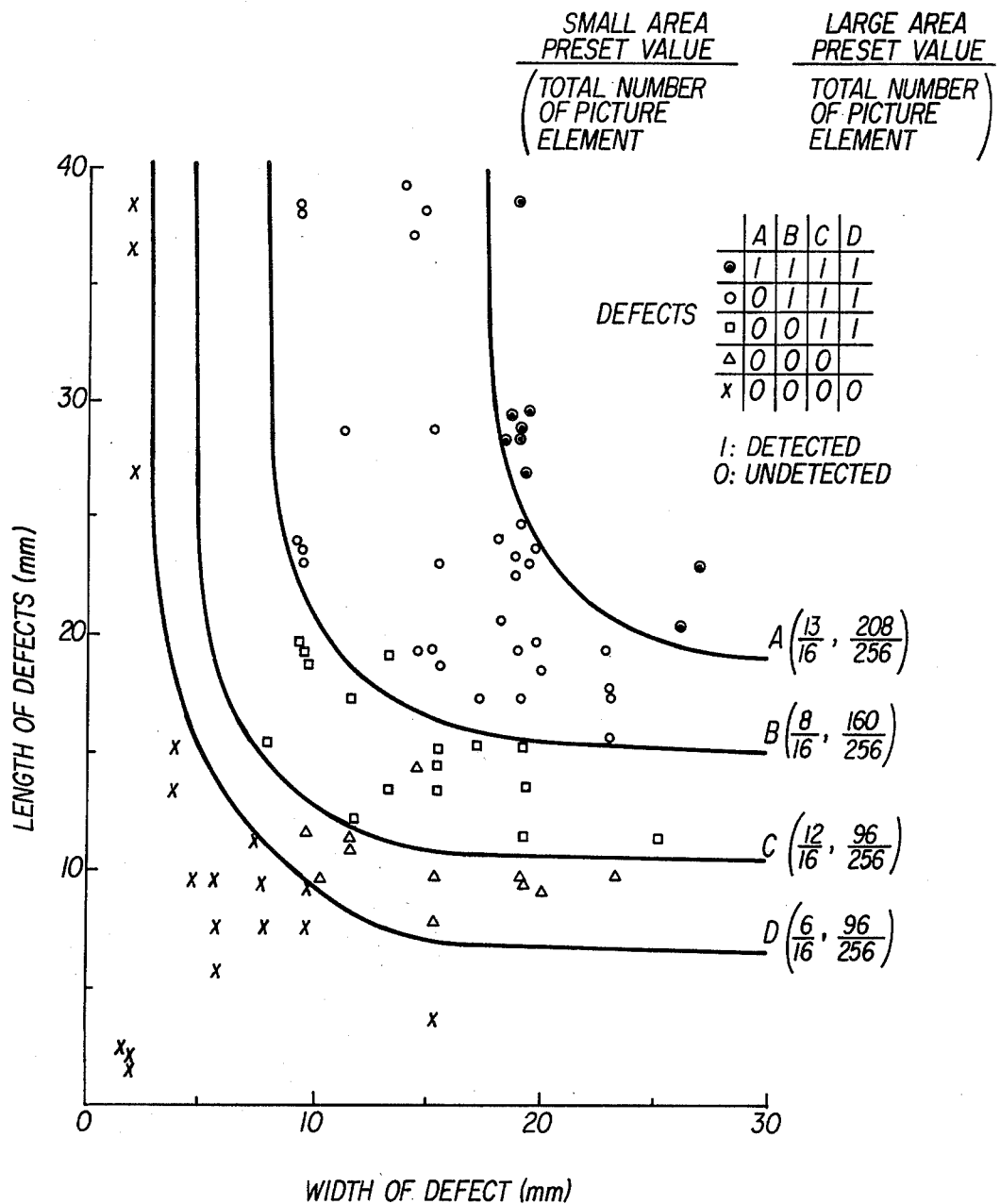
FIG. 12 is a graphic representation of the relation between dimensions of surface imperfections and ranges of detection.

FIG. 12 shows the results of experiments inspecting a radiant hot steel slab by the dual-area analysis according to the present invention. When the critical values for the small and large area were in the A setting (small area=13/16, large area=208/256), only the defects of the mark ◉ were detected. In the B setting, the defects of the marks ◉ and ○ were detected. In the C setting, the defects of the marks ◉, ○ and □ were detected. In the D setting, the defects of the marks ◉, ○, □ and △ were detected.

It will be understood from the foregoing description that the dual-area analysis of the data of picture elements completely removes the noises of scales, allowing the extraction of defects alone and judgement on the nature of the defects according to the areas of the individual defects.

Figure 13:
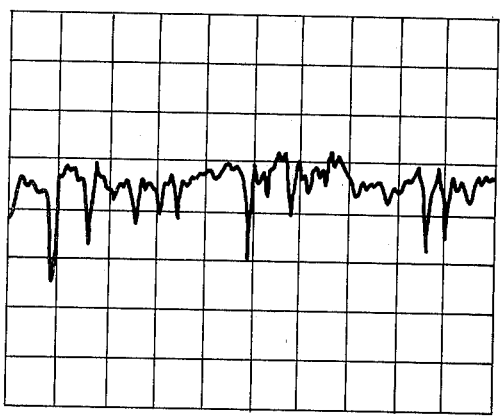
FIG. 13 is an illustration of a wave form of a scale.
Figure 14:
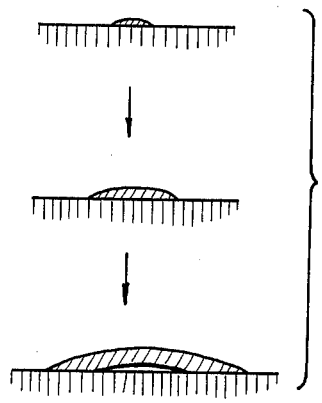
FIG. 14 is a diagrammatic view illustrating generating and cooling stages of a scale.

Upon comparing an image of hot radiant material with the distribution of actual surface defects as viewed at room temperature, it has been found that the wave form of the signal corresponding to a scale is generally narrow as shown in FIG. 13. Sometimes it comes out in a greater width but in such a case it drops deep (dark), suggesting correlation between its width and depth and with the physical changes which a scale undergoes in the growing and cooling stages as shown in FIG. 14. More particularly, a scale consists of layers of $FeO$, $Fe_3O_4$ and $Fe_2O_3$ from its inner to outer side, and in the initial stage or when it is very small, it barely cools off due to good adhesion to the steel strip. As the scale grows gradually into a larger size, it comes off the steel strip due to unbalanced growth of the respective layers. The more it peels off, the more the heat conductivity between the scale and the steel strip is diminished, the scale cooling off since now it is unable to restore heat. A scale of a larger size peels and cools off to a greater degree and appears darker.

Figure 15:
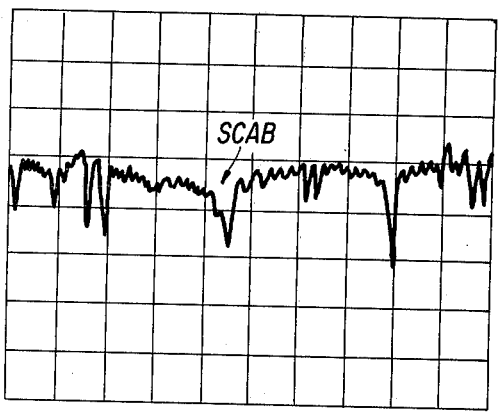
FIG. 15 is an illustration of a wave form of a scab.
Figure 16:
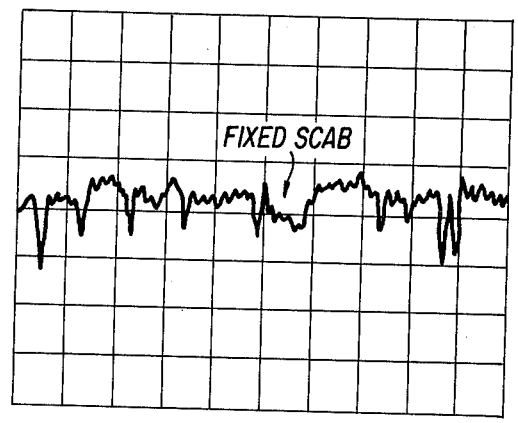
FIG. 16 is an illustration of a wave form of a scab with a higher degree of defectiveness.

On the other hand, the wave form of the signal corresponding to a scab is generally broad as shown in FIG. 15. The wave form of a objectionable or fixed scab is relatively small in depth (less dark) as shown in FIG. 16. Namely, fixed scabs are slow in cooling. In contrast, the wave form of a partly peeled, less objectionable scab is deeper since it cools off more quickly. Large scabs generally have larger dark areas.

Figure 17:
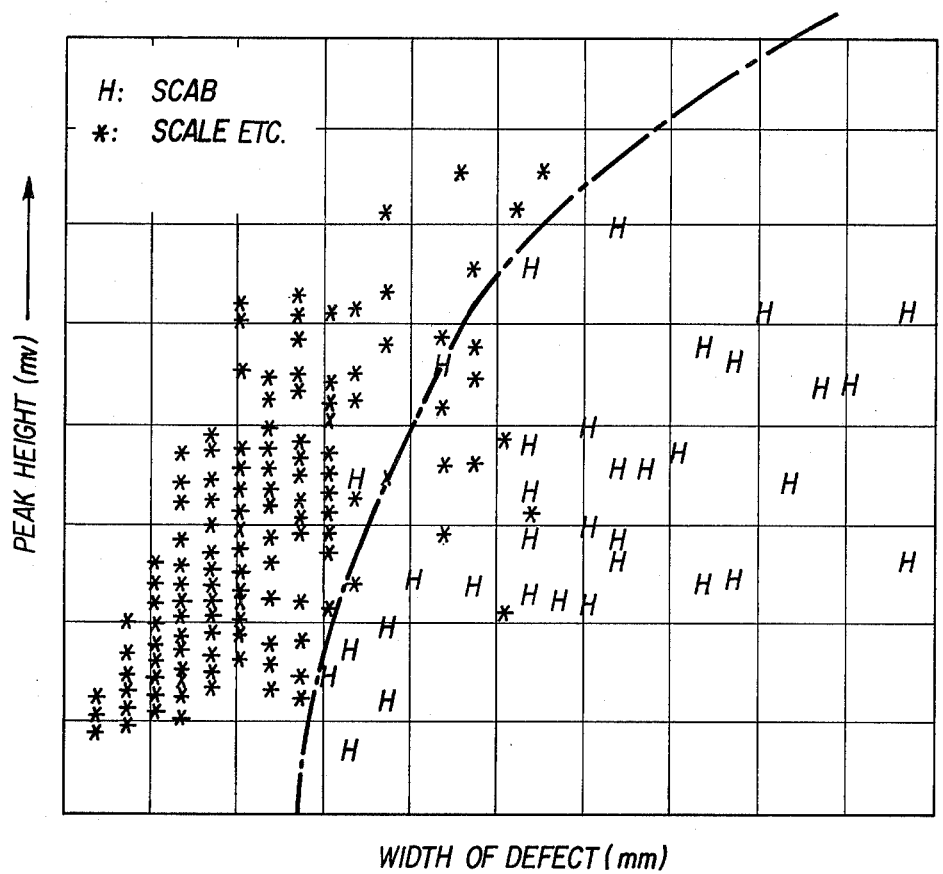
FIG. 17 is a graphic representation of the distributions of depths and widths of signals.

In order to ascertain whether the width and depth of video signal wave form can be used as parameters in discriminating scabs from scales and judging the objectionable degree of detected scabs, about 500 scales and 30 scabs were plotted on a graph (FIG. 17). As a result, it has been found that there is relatively strong correlation between width and depth of the scales wave forms, that scabs are clearly distinguishable from scales and that scabs of unacceptable or objectionable quality appear in a particular range. Therefore, by setting in the signal processing system a functional relation which defines defectiveness by way of the width and depth of the received video signals, it becomes possible to obtain outputs which determine whether a detected surface defect is of a passable quality.

In the signal processing operation, those of the received video signals which are lower than a predetermined normal level Po are extracted respectively to calculate their depths P and widths W and whether they are acceptable or not is judged on the basis of the combination of the parameters P and W. To this end, a data map for the combinations of the parameters P and W is prepared by correlating video signals of various P-W combinations as obtained from at least one steel strip with actual conditions of the corresponding surface portions. On the basis of the data map thus obtained, the discriminant value is defined by the following defect discriminant equation:

$$f(P, W) = \frac{W}{\alpha + \{\beta(P - P_0)^\gamma\}}$$

in which $\alpha$, $\beta$ and $\gamma$ are experimentarily determined beforehand. When $f(P,W) \geq 1$, the signal is judged as "defective" and when $f(P,W) < 1$, the signal is judged as "non-defective". In the discriminating operation, the values of the parameters P and W of the video signals to be judged are substituted into the equation given above.

Figure 18:
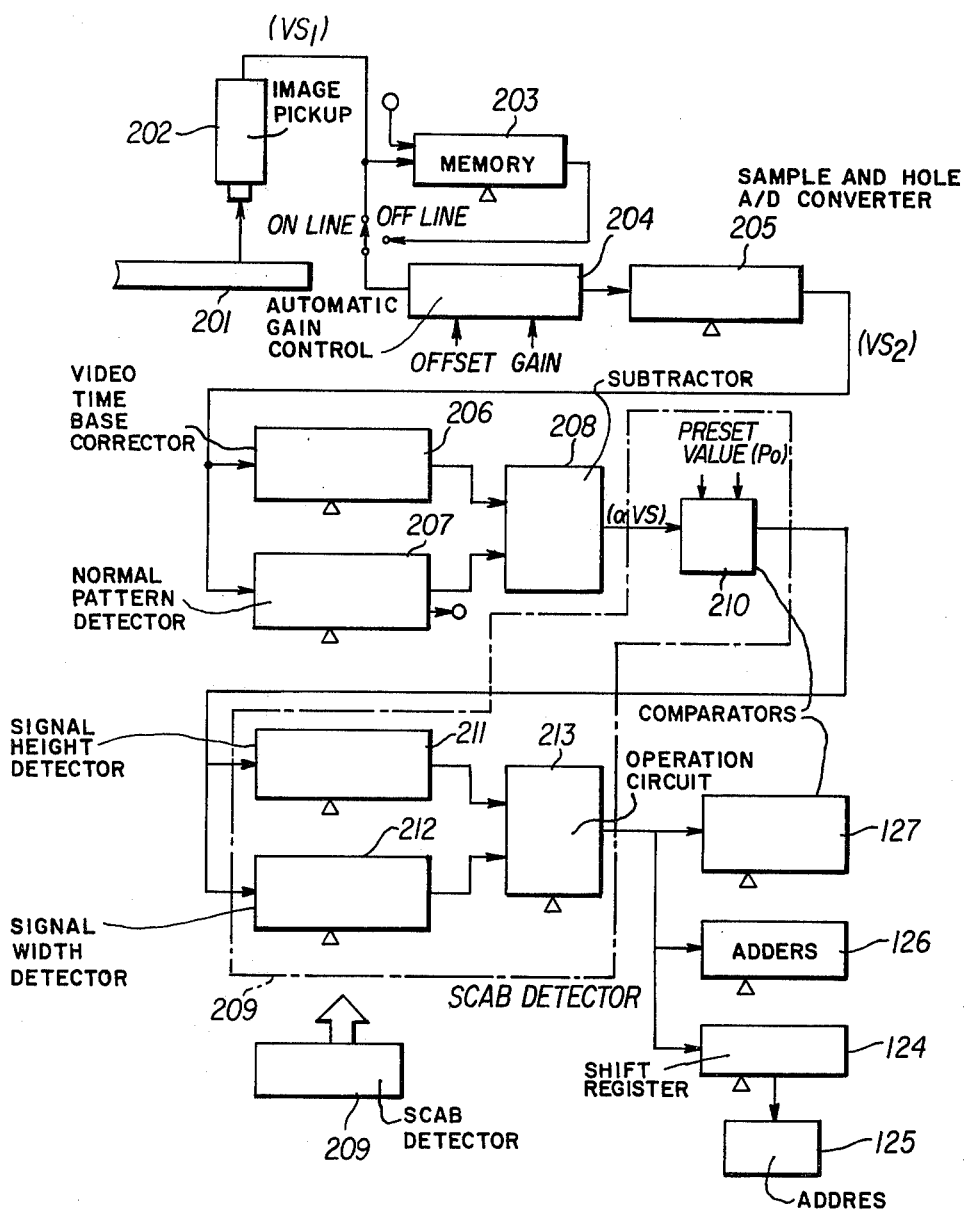
FIG. 18 is a block diagram of a flaw detector by depth and width of signals.
Figure 19:
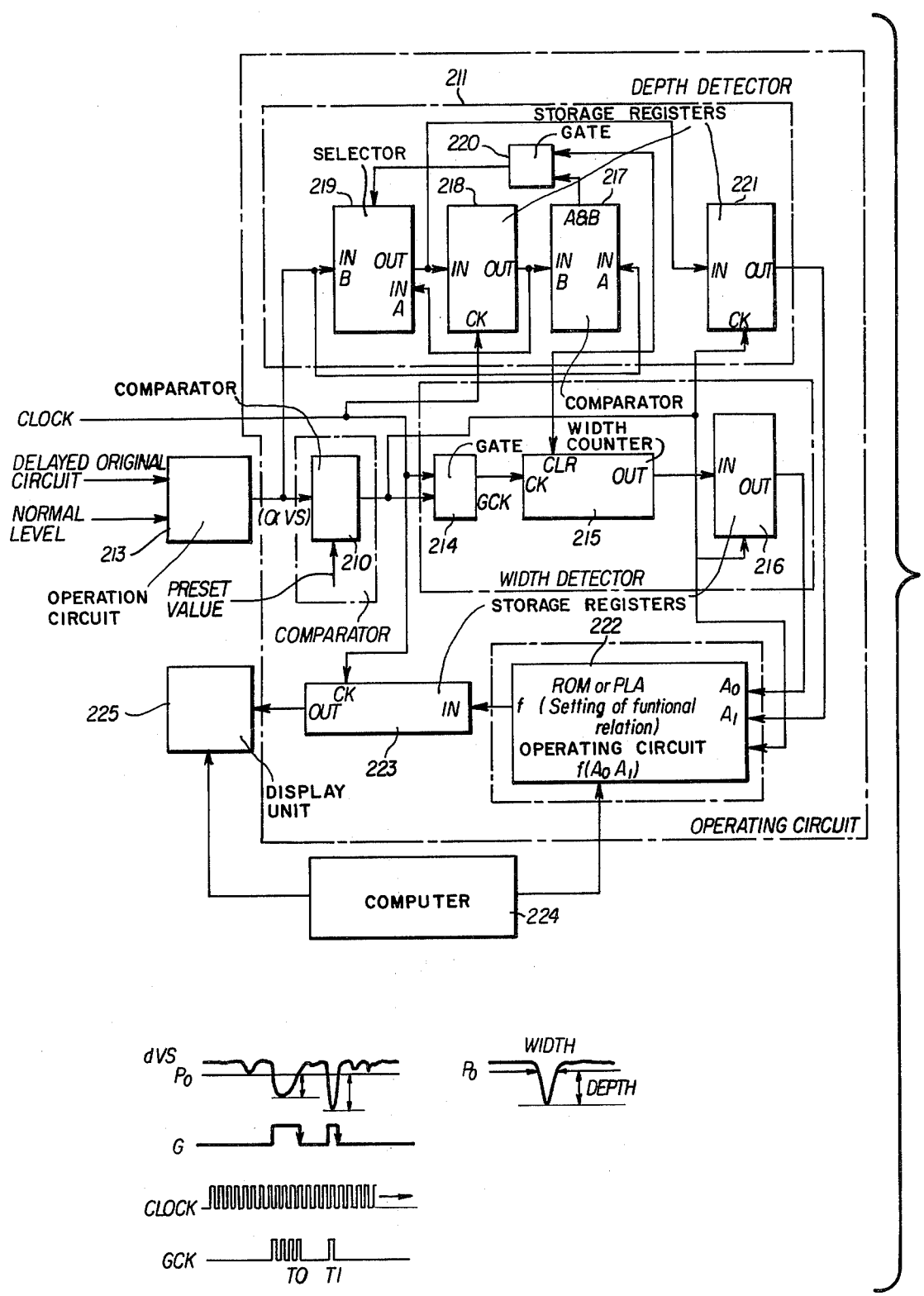
FIG. 19 is a block diagram of a scab discriminator.

Reference is now made to FIGS. 18 and 19 which illustrate a system for carrying out the above-described signal processing method. FIG. 18 is a block diagram of the signal processing system as a whole and FIG. 19 is a block diagram of a discriminant circuit which forms an important part of the system.

Referring to FIG. 18, the video signal $VS_1$ produced by an electro-optics pickup device 202 which picks up the image of a hot radiant steel strip 201 is fed to memory 203 and at the same time to a sample and hold circuit analog to digital converter 205 through an automatic gain control 204 thereby to convert the video signal $VS_1$ into a digital signal $VS_2$. The digital signal $VS_2$ is fed to a delay line video time-base corrector 206 and to a normal pattern detector 207 which produces a normal level signal at its output. Subtraction circuit 208 produces a deviation signal $\alpha VS$ indicative of the difference of the original video signal from the normal level signal. The deviation signal $\alpha VS$ is fed to a scab detector 209 which consists of a comparator 210, a signal height detector 211, a signal width detector 212 and an operation circuit 213. Scab detector 209 compares the deviation signal $\alpha VS$ with the predetermined level $P_0$ by comparator 210. Signal width detector 212 includes a gate 214, a width counter 215 and storage registers for width 216 as shown in FIG. 19 and counts clock pulses for a time duration in which the deviation signal $\alpha VS$ falls beneath the predetermined level signal $P_0$, temporarily storing the width W of the signal of a scab or scale in the storage registers 216. Signal depth detector 211 includes comparator 217, storage registers 218, selector 219, gate 220 and storage registers for signal height 221 as shown in FIG. 19. The deviation signal $\alpha VS$ from comparator 210 is also fed to the signal depth detector 211, which sequentially calculates the pit value P of the deviation signal for a time duration in which the deviation signal $\alpha VS$ is smaller than the predetermined level $P_0$, storing the result temporarily in storage register 221. If the deviation signal $\alpha VS$ becomes greater than the predetermined value $P_0$, the gate signal G turns to binary logic 0 and, on the negative-going edge of the gate signal, P and W are read out from the storage registers 221 and 216, respectively, and fed to the address input of a PROM (programable read only memory) of an operation circuit 222. On the other hand, the gate signal is fed directly to the read-out terminal of the PROM, so that the data of function $f(P,W)$ which has been stored beforehand in the PROM as defect data is storage in the storage registers 223 on the negative-going edge of the gate signal. This discrimination may be performed by storing the discriminant data in PROM as in the "EXPERIMENT 1" which is given hereinafter, or by the PLA (programable logic array) or the multi-function operator (for analog signal). In this manner, upon receiving a signal of a scab or scale, an output in a value comparable to a degree of defectiveness can be produced in real-time, namely, within one clock time from termination of the input signal. The result of the operation is transmitted to computer 224 through storage registers 223 and, after calculation of the total area of defects and higher judgements such as discrimination by positions of defects, is fed to display unit 225, monitor 226 and printer 227 and used for external control.

This signal processing system completely solves the conventional problem wherein it is difficult to discriminate scabs on the radiant image of the hot steel strip simply by the amplitude of the signals due to the diversity in size and tone which is attributable to the unique generating mechanism mentioned hereinbefore. The outstanding effects of this signal processing method are shown more particularly in FIGS. 20 and 21.

Figure 20:
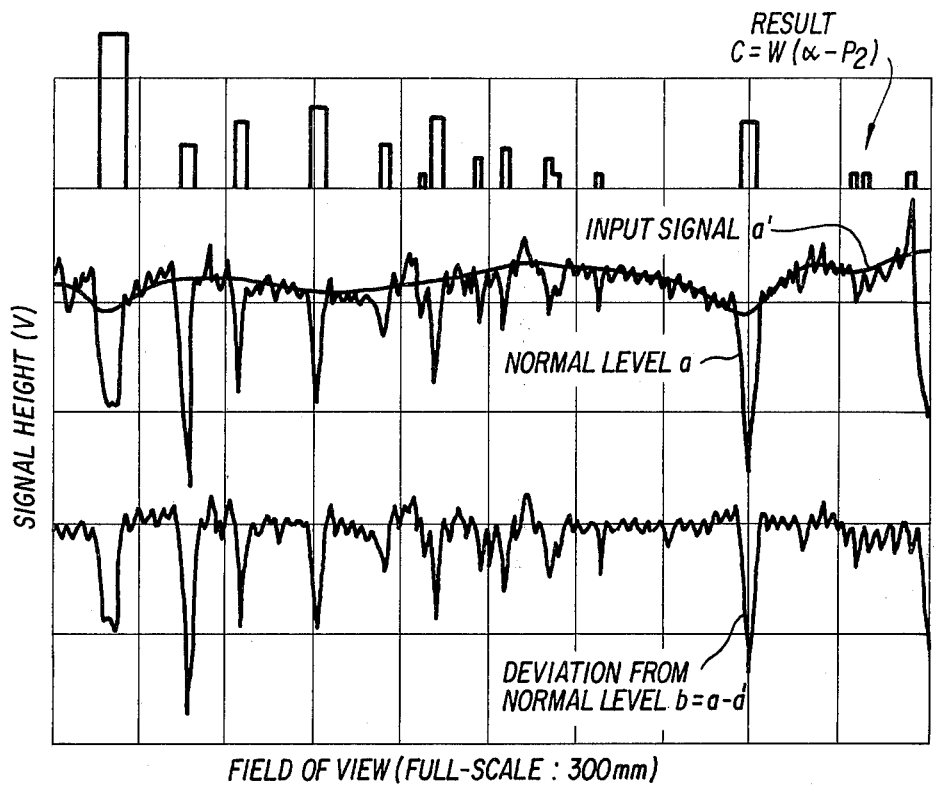
FIGS. 20 and 21 are illustrations of various wave forms.
Figure 21:
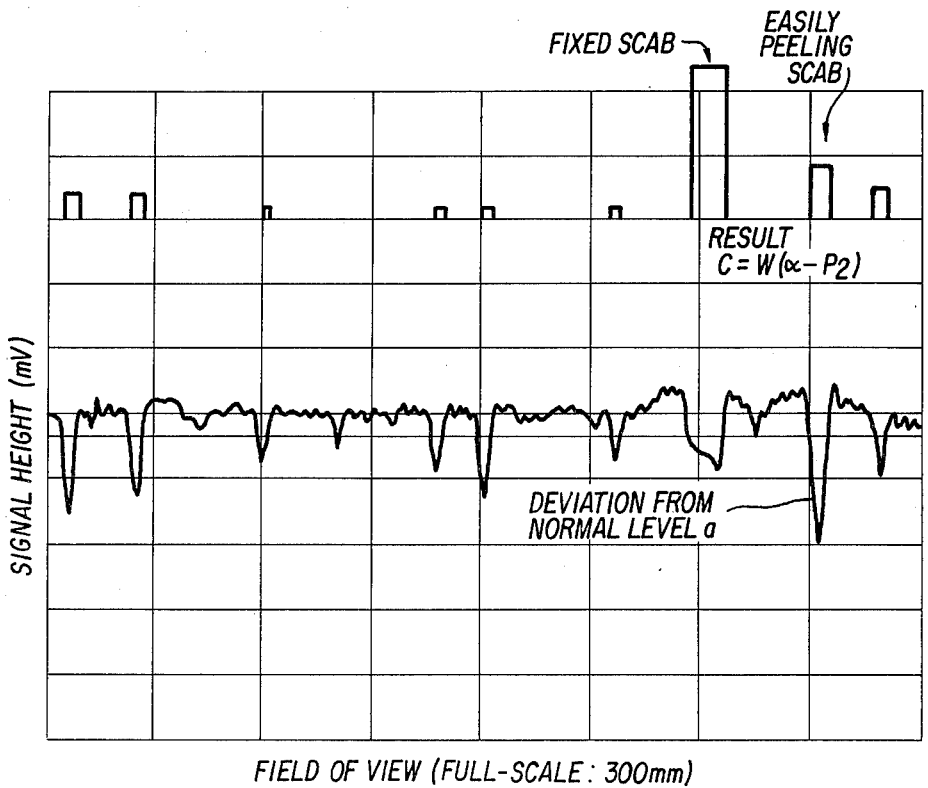

In FIG. 20, there is shown a normal level signal a' which is obtained from a video signal of a radiant light image shown at a, along with a deviation signal b indicative of the difference between the signals a' and a. Indicated at c are the results obtained by the above-described signal processing operation, in which the scales are sufficiently suppressed while the scabs appear in an emphasized form. In the case of a radiant light image which contains fixed scabs of a higher degree of defectiveness and partly peeled scabs of a lower degrees due to defectiveness including a large number of scales as shown at a of FIG. 21, outputs giving opposite degree of defectiveness and with noises of scales would be produced if based solely on the darkness (depth) of the signals. On the other hand, if based solely on the width of the signals, it would be difficult to indicate precisely the degree of defectiveness of the surface imperfections, in contrast to the outputs at c of FIG. 21 which come out in proportion to the degree of defectiveness.

EXPERIMENT 1

Hot steel material: Slab (capped steel)
Steel temperature: 1150° C. (as measured at the center of top surface)
Electro-optics pickup device: 2048-bit solid state image sensor

Procedures

Figure 22:
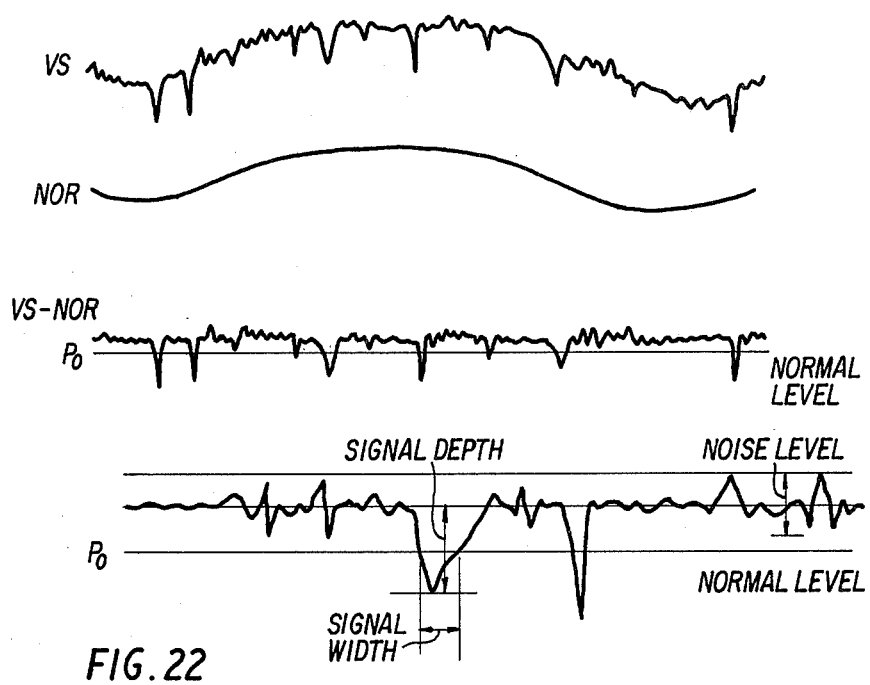
FIG. 22 is an illustration of wave forms occurring in EXPERIMENT 1.
Figure 23:
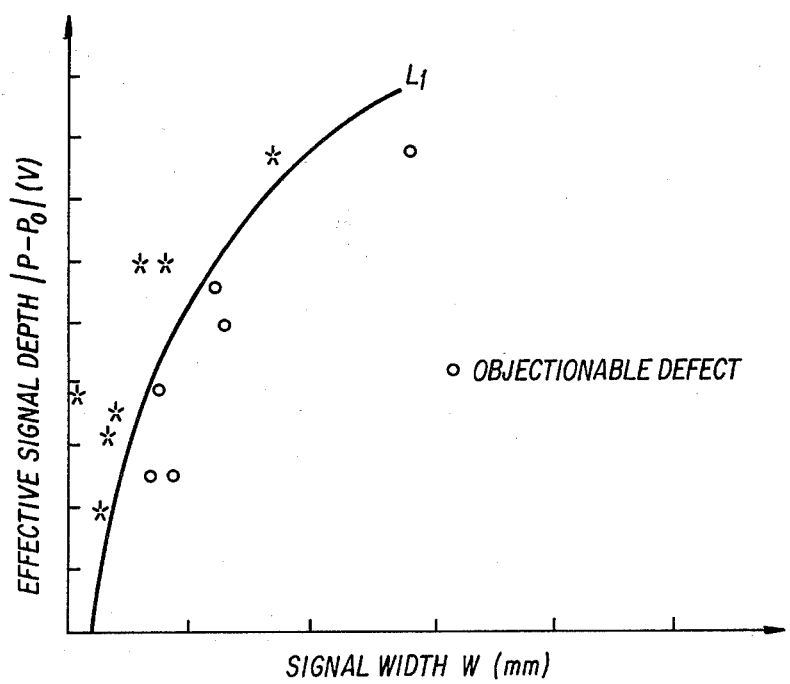
FIG. 23 is a defect data map for obtaining discriminating curve $L_1$.

The video signals of the radiant light image of the hot steel slab taken by the solid state image sensor were fed through an amplifier and an automatic gain control to a high-speed sample and hold analog to digital converter for conversion into 8-bit digital signals VS. The digital signals were, on one hand, passed to the process for two-dimensional peak hold and averaging over a predetermined area for extracting normal level signals NOR which followed the uneven temperature distribution inherent to the steel material. On the other hand, the digital signals were delayed through shift registers for the time necessary for the extraction of the normal level signals NOR. Deviation signal $\alpha VS$ was obtained by subtraction of the normal level signal from the delayed digital signal and those portions of the deviation signal $\alpha VS$ which fell beneath predetermined level $P_0$ ($= -0.1$ V), which was determined in consideration of noise level ($\lesssim 50$ mV), were taken out to calculate the depth P (V) and width W (mm) of the respective signals (see FIG. 22). Several signals which included scabs and scales were sampled out and checked for their degree of defectiveness in terms of the combination of parameters (P,W). FIG. 23 shows a map of the defect data for 6 scabs and 7 scales which were sampled out in this manner. The parameters, P, W and in the discriminating curve $L_1$ $$\frac{W}{\alpha + \{\beta(P - P_0)\}^\gamma} = 1$$

which separated the colonies of the scabs and scales were determined. In this case, $\alpha=2$, $\beta=7.5$, $\gamma=2$. By substituting these, a discriminating equation was obtained $$f(P, W) = \frac{W}{2 + \{7.5(P - P_0)\}^2} \quad (4)$$

$f(P, W) \geq 1$ : "Defective"
$f(P, W) < 1$ : "Non-defective"

Figure 24:
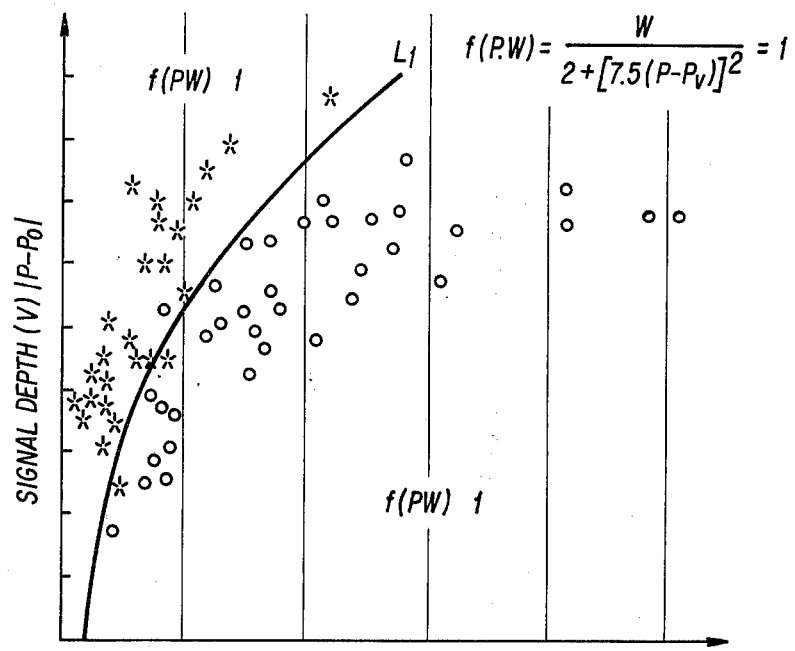
FIG. 24 is a graphical representation of the discrimination of defects by curve $L_1$.

In this manner, once the discriminating equation (4) was determined, scabs on steel strips of the same kind could be discriminated automatically simply by substituting into equation (4) the value of the combination of parameters (P, W) which was calculated by the above-described method. In the practical operation, the contents of equation (4) are given in the form of a data output from the PROM which receives the values of P and W at the address terminals thereof to discriminate the signals as graphically illustrated in FIG. 24. A discriminating operation dealing with 62 combinations of the parameters (P, W) calculated from newly received video signals resulted in a detection rate as shown in the Table below which was far higher than the rate which would be obtained by the conventional detection method based on the signal depth or width alone.

TABLE

| Detection rate | 97.2% |
|---|---|
| Misdetection | 2.8% |
| Over-detection | 7.7% |

EXPERIMENT 2

Figure 25:
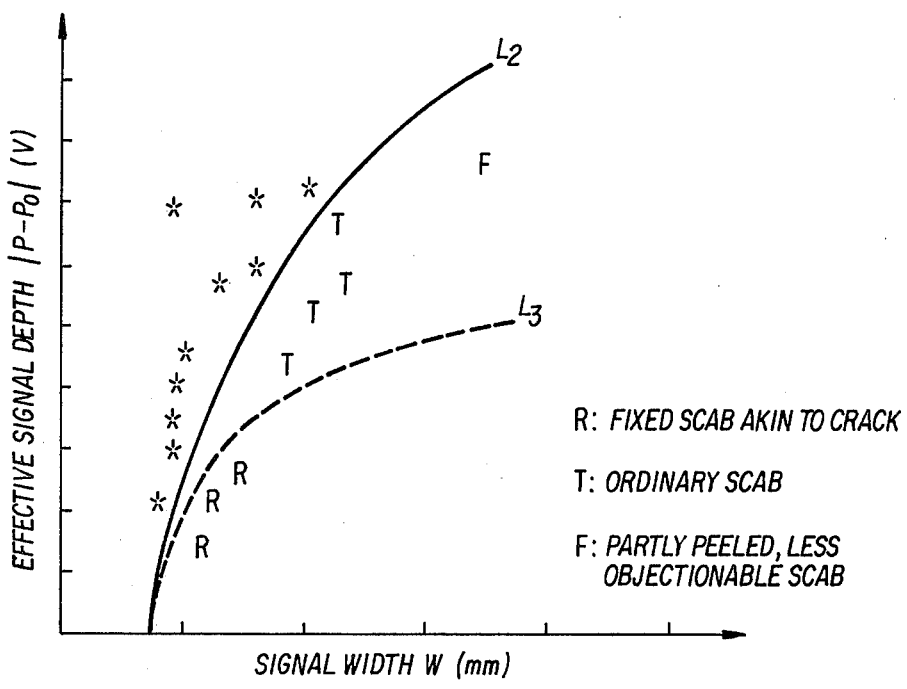
FIG. 25 is a defect data map for obtaining discriminating curve $L_2$ in EXPERIMENT 2.

Hot steel material: Slab (semi-killed steel)
Steel temperature: 1200° C. (as measured at the center of top surface)
Electro-optics pickup device: 2048-bit solid state image sensor Procedures The depth P (V) and width (mm) of signals were calculated in the same manner as in EXPERIMENT 1. Several scabs and scales were sampled out to prepare a data map (FIG. 25), including 10 scales and 8 scabs (3 R-type scabs, 4 T-type scabs and 1 F-type scab). Based on this distribution of scales and scabs, the parameters $\alpha$, $\beta$ and $\gamma$ in the discriminating curve $L_2$ $$\frac{W}{\alpha + \{\beta(P - P_0)\}^\gamma} = 1$$

were determined. In this case, $\alpha=7.5$, $\beta=7.5$ and $\gamma=2$, so that $$f(P, W) = \frac{W}{7.5\{7.5(P - 0.1)\}^2}$$

$f(P, W) \geq 1$ : "Defective"
$f(P, W) < 1$ : "Non-defective"

Figure 26:
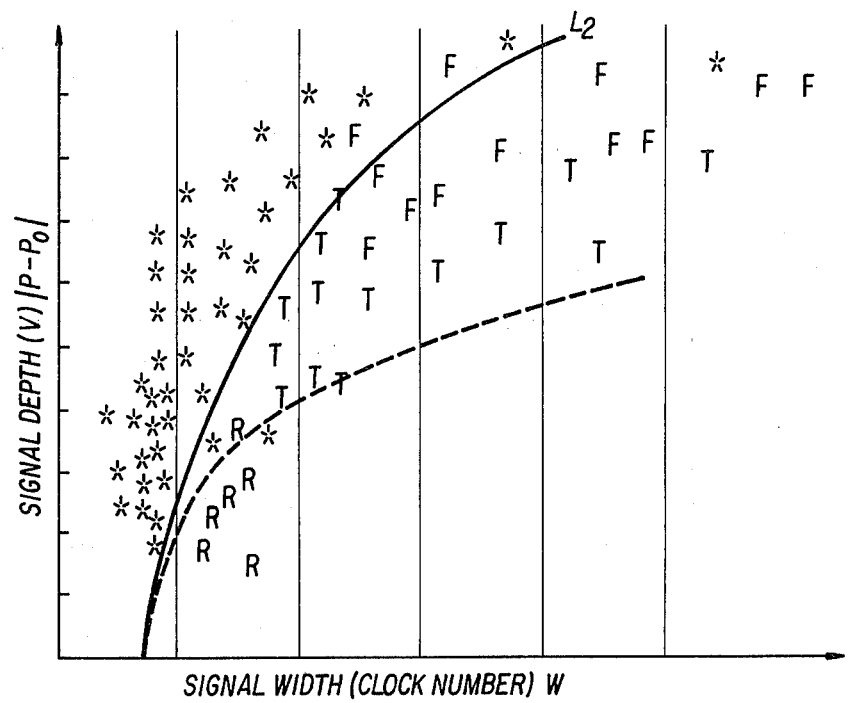
FIG. 26 is a graphical representation of discrimination of defects by curves $L_2$ and $L_3$.

This signal discrimination by the equation (5) is shown graphically in FIG. 26. The scab signals were clearly discriminated from scale signals, attaining a high detection rate as in EXPERIMENT 1. In addition, by using a discrimination curve $L_3$ of FIG. 25, it becomes possible to distinguish the R-type fixed scabs of a high degree of defectiveness akin to cracks from ordinary scabs of the T-type and from partly peeled scabs of the F-type, giving judgements counting for the degree of defectiveness.

Figure 28:
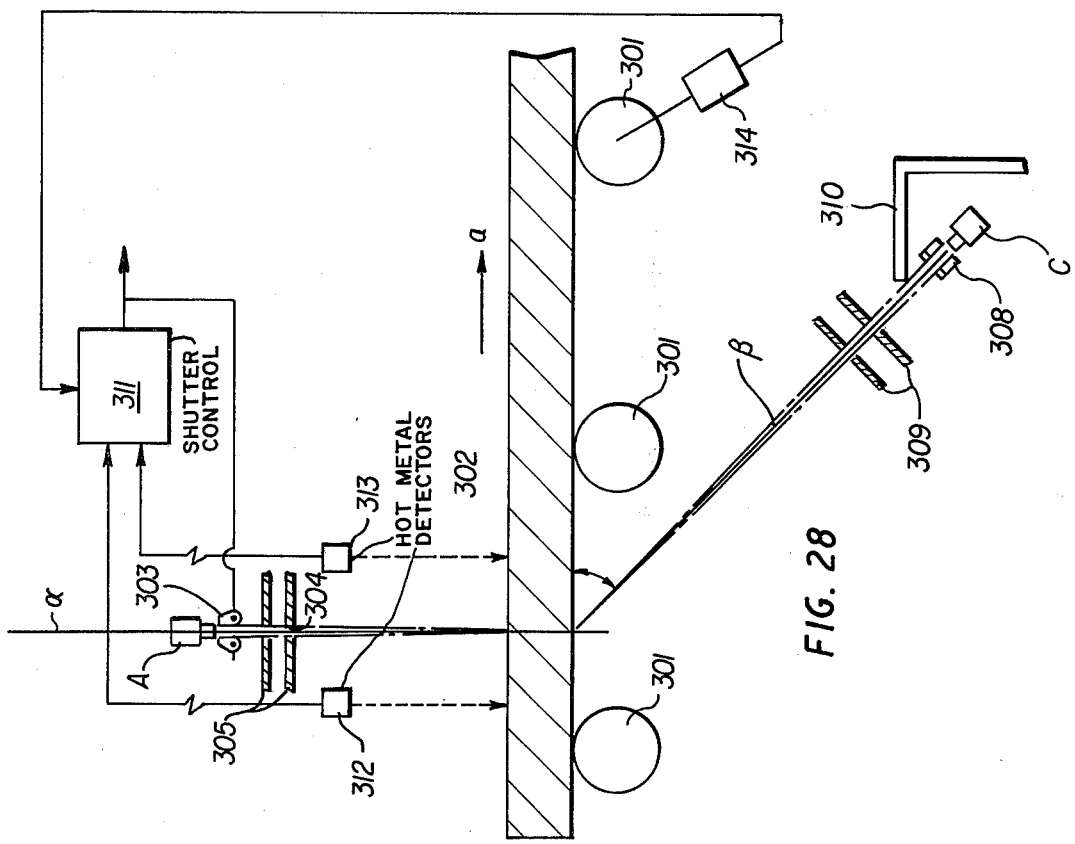
FIG. 28 is a diagrammatic side view of the system of FIG. 27.
Figure 27:
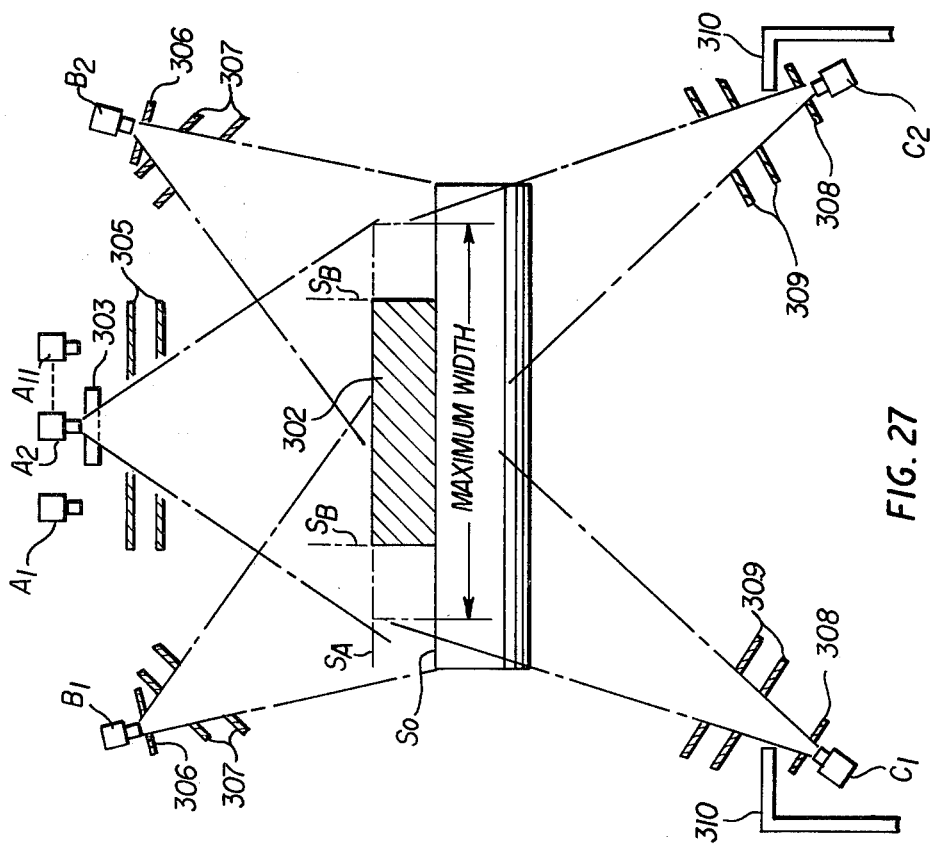
FIG. 27 is a diagrammatic front view of a multi-camera surface inspection system.

FIGS. 27 and 28 illustrate the multi-camera surface inspection system mentioned hereinbefore, in which a hot radiant material 302 to be inspected is transported in the direction of the arrow a along a transfer passage which is constituted by a roller conveyor 301. Indicated at $A_1$ to $A_n$ are top line scan cameras which are located overhead the transfer passage in a plane $\alpha$ perpendicular to the direction of travel of the material 302 and directed perpendicular to the travel direction to scan a line of intersection $S_A$ of the plane $\alpha$ with the top surface of the material 302. Beneath the top line scan camera A, there is provided a shutter 303 and, beneath the shutter 303, a multi-covering heat shield 305 with a slit 304 of dimensions corresponding to or greater than the view field of the top line scan camera A. Designated at $B_1$ and $B_2$ are side line scan cameras which have a focusing depth of field greater than the thickness of the inspecting material 302 and a tilted alignment of the optical components. The side line scan cameras are located on opposite sides of and in the same plane $\alpha$ as the top line scan camera A and directed inwardly toward the side surfaces of the material 302 to scan obliquely from above the opposite end portions of the line of intersection $S_A$ of the top surface 302 of the material with the plane $\alpha$ and the lines of intersection $S_B$ of the plane $\alpha$ with the side surfaces of the material 302. A multi-covering heat shield 307 and a shutter 306 are also provided beneath the side line scan cameras $B_1$ and $B_2$. Denoted at $C_1$ and $C_2$ are lower line scan cameras which are located in the positions beneath and on the outer sides of the transfer passage and in a plane $\beta$ which contains the line of intersection $S_C$ of the plane $\alpha$ with the bottom surface and which is slanted downward in the direction of travel of the material 302. The lower line scan cameras $C_1$ and $C_2$ scan obliquely from beneath the line of intersection $S_C$ of the plane $\alpha$ on the bottom surface of the material 302 with an angle of elevation of about 30° to 60°. Similarly to the top and upper line scan cameras, the lower line scan cameras $C_1$ and $C_2$ are provided with shutters 308 and multi-covering heat shields 309. The lower line scan cameras $C_1$ and $C_2$ are further provided with hoods 310 for protecting them against scales or other scraps which drop from the bottom surface of the material 302. A shutter control 311 is arranged to open the shutters 303, 306 and 308 when the leading end of the material 302 is detected by a hot metal detector 312 and close them upon detection of the terminal end of the material 302 by the hot metal detector 313. The shutter control 311 also closes the shutters 303, 306 and 308 when the transfer of the material is stopped, detecting the stop by a rotation detector 314.

Figure 30:
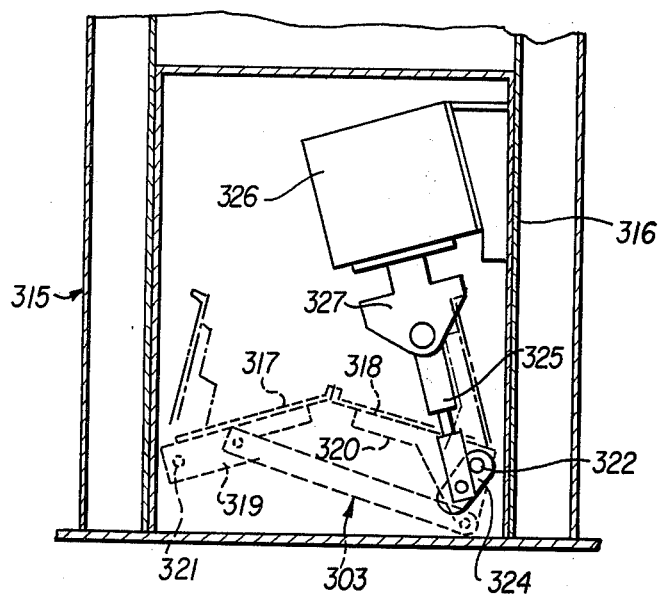
FIG. 30 is an enlarged sectional view taken on line A—A of FIG. 29.

As shown in FIGS. 29 and 30, the shutter 303 is housed in a water jacket 315 through which cooling water is passed. More particularly, the water jacket 315 receives therein a shutter case 316 in which a pair of shutter plates 317 and 318 are pivotally supported on axes 321 and 322 by arms 319 and 120, respectively, for opening and closing operations. The shutter arms 319 and 320 are interconnected by a link 323 to be driven together. One end of the axis 322 is connected to a movable core 327 of an electromagnet 326 through an arm 324 and a link 325 so that, upon exciting the electromagnet 326, the shutter plates 317 and 318 are turned about the respective axes 321 and 322 into the open positions shown in phantom in FIG. 30. Indicated at 328 is a glass sheet which is fitted in the top wall of the shutter case 316. The top line scan cameras A are mounted on top of the cooling water jacket 315 through an angle adjustor mechanism 329 and sheltered under a top cover 330.

As shown in FIG. 31, the shutter 306 is provided with a pair of shutter plates 332, an electromagnet 333 and a shutter case 334 which are mounted in a cooling water jacket 335 in the same manner as in shutter 303 except that a window 336 of the shutter case 334 is provided in a plane which perpendicularly intersects the axis of the obliquely mounted side line scan camera B. Denoted at 337 is an angle adjustor mechanism and at 338 a top cover.

Figure 34:
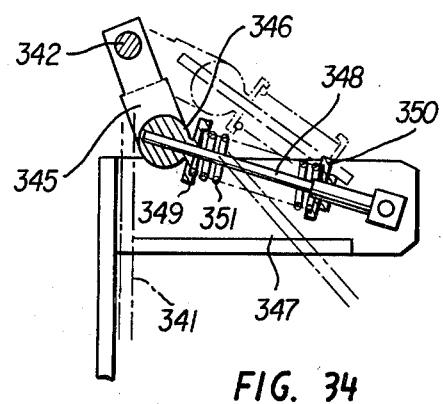
FIG. 34 is a diagrammatic enlarged view of a shutter biasing mechanism.
Figure 32:
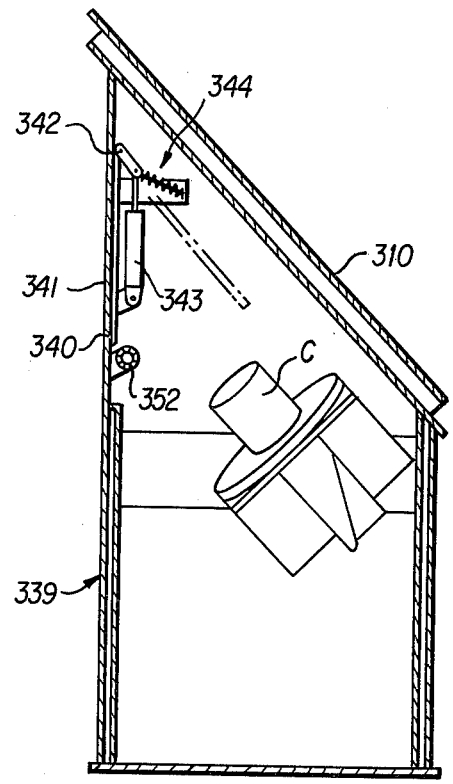
FIG. 32 is a diagrammatic sectional view of a lower line scan camera and its shutter.

Referring to FIGS. 32 to 34, the shutter 308 for the lower line scan camera C is provided with a shutter plate 341 which has its upper side pivotally supported on an axis 342 to close a window in the wall of a cooling case 339 which accommodates the camera C, and with a cylinder which operates to open and close the shutter plate 341. The shutter 341 is biased into the closed position by a spring-loaded biasing mechanism 344 which is, as shown in FIG. 34, constituted by an arm 345 which is fixedly mounted on the shutter axis 342, a rotary member 346 which is rotatably mounted on the arm 345, a rod 348 which has one end thereof pivotally supported on a fixed bracket 347 and the other end slidably inserted into a bore in the rotary member 346, and a compression spring 351 which is interposed between the spring seats 349 and 350 on the rod 348. The reference numeral 352 indicates an injection pipe which is provided for forming an air curtain. The protective hood 310 is mounted slantingly on the cooling case 339 and provided with suitable shock absorbing material on the underside thereof.

Since the top surface of the material is swept perpendicularly by the top line scan camera, the resolution of the top surface is improved to a remarkable degree. The side scan cameras are adapted to sweep obliquely from above the top and side surfaces of the material across the opposite corner edges thereof so that surface imperfections in the corner portions which would otherwise often become dead zones can be detected reliably. In addition, the side line scan cameras which are located in the positions obliquely above the transfer line can always hold the inspecting material in the viewing field even in the event of digressive movements of the material occurring due to variations in the width or changes in the travel position or meandering movements of the material, with the listed alignment of optical component serving to view the material within the focusing depth of field and at a constant magnification. The lower line scan cameras with the protective hoods are located to scan the bottom surface of the material for defects obliquely from beneath without having the respective view field blocked by the protective hood. In a case where the lower line scan cameras are located in positions appreciably on the outer sides of the transfer passage, it is possible to reduce the possibility of the cameras being directly attacked by falling scales or other particles and to inspect the lower corner portions of the material. The lower line scan cameras are also provided with a tilted alignment of the optical components so that the parallax of the image resulting from the oblique viewing of the bottom surface can be corrected. The use of the line scan type camera is preferred since it can be located behind a multi-covering heat shield to avoid the strong heat radiation of the material, inspecting the material surface through an extremely narrow slit which is provided in the multi-covering heat shield.

Figure 35:
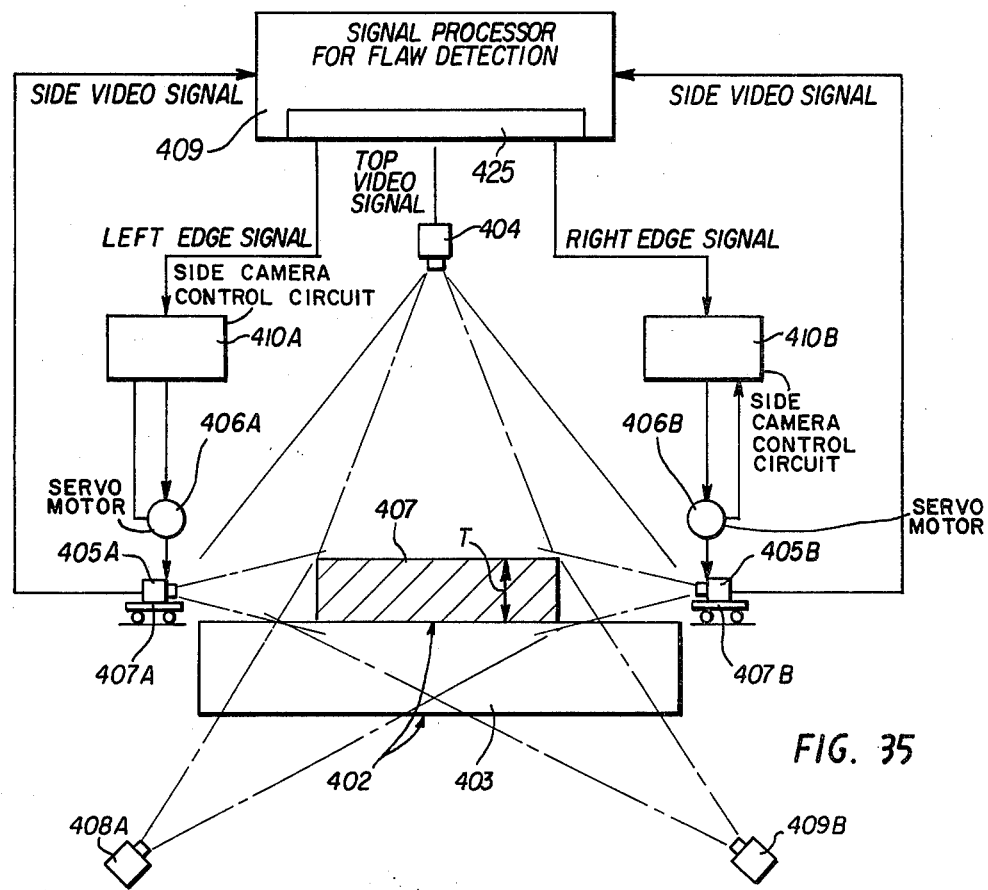
FIG. 35 is a diagrammatic view of a camera follow-up control device.
Figure 36:
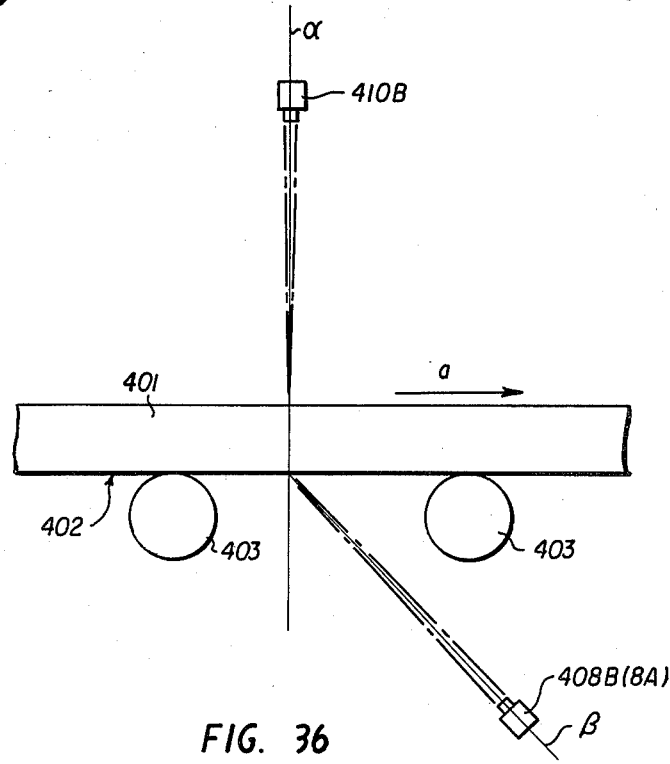
FIG. 36 is a diagrammatic side view of top and lower cameras.
Figure 37:
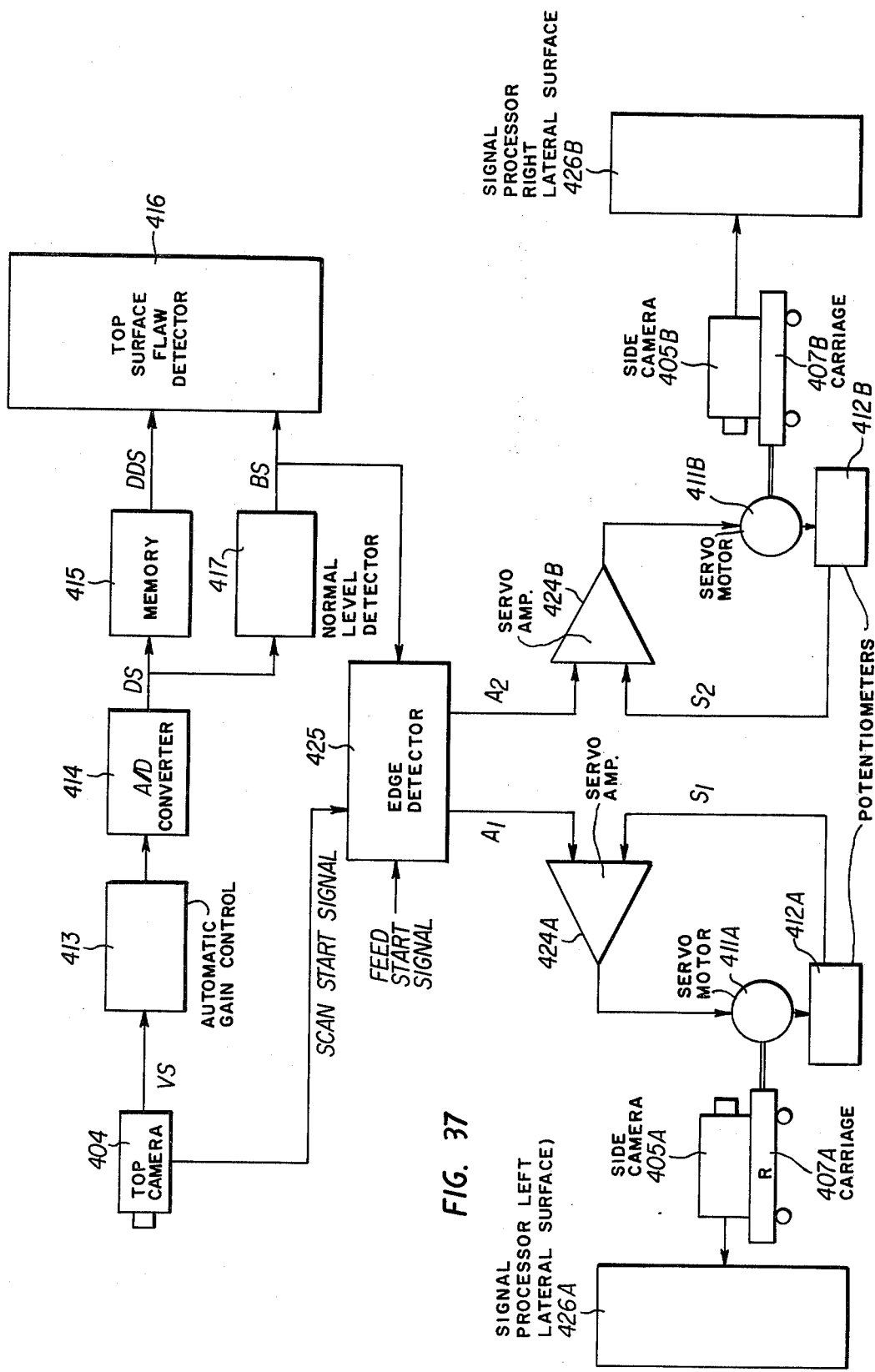
FIGS. 37 and 38 are block diagrams of the camera of circuit arrangements camera follow-up control device.
Figure 38:
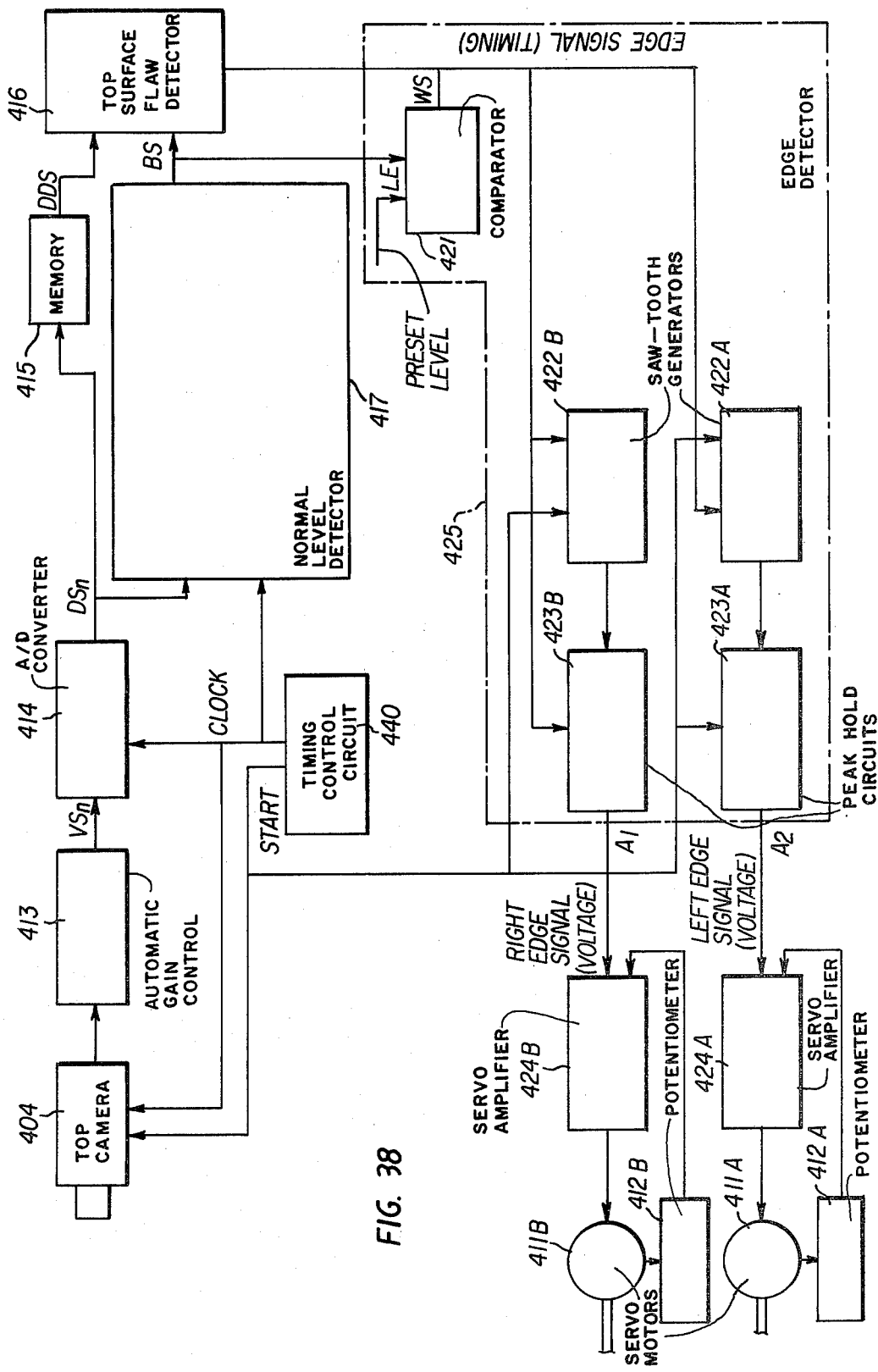

FIGS. 35 to 40 illustrate an embodiment in which the afore-mentioned normal level signals BS are used for detecting the edges of a hot conveyed material in controlling the movable side cameras in such a manner as to follow digressive movements of the conveyed material. Referring to FIGS. 35 and 36, overhead a transfer passage 402 having a conveying means such as a roller conveyor 403 for transferring therealong a hot radiant material 401 to be inspected, there is provided a top camera 404 similarly in a plane $\alpha$, which is disposed perpendicular to the travel direction of the material 401, to scan the top surface of the material in a direction perpendicular to the travel direction of the material. Indicated at 405A and 405B are a pair of side cameras which scan the opposite lateral surfaces of the material 401. In this embodiment, the side cameras 405A and 405B are mounted on carriages 407A and 407B, respectively, which are movable toward and away from the material 401 by means of servo motors 406A and 406B. As in the foregoing embodiment, the lower cameras 408A and 408B are located beneath the transfer passage 402 to scan across the bottom surface of the material 401 obliquely from beneath in a plane $\beta$ slanting downward in the travel direction of the material. Indicated by block 409 is a signal processor for the detection of surface defects, which is arranged as shown in FIGS. 37 and 38. The reference numerals 410A and 410B denote side camera control circuits including servo amplifiers 411A and 411B.

Figure 39:
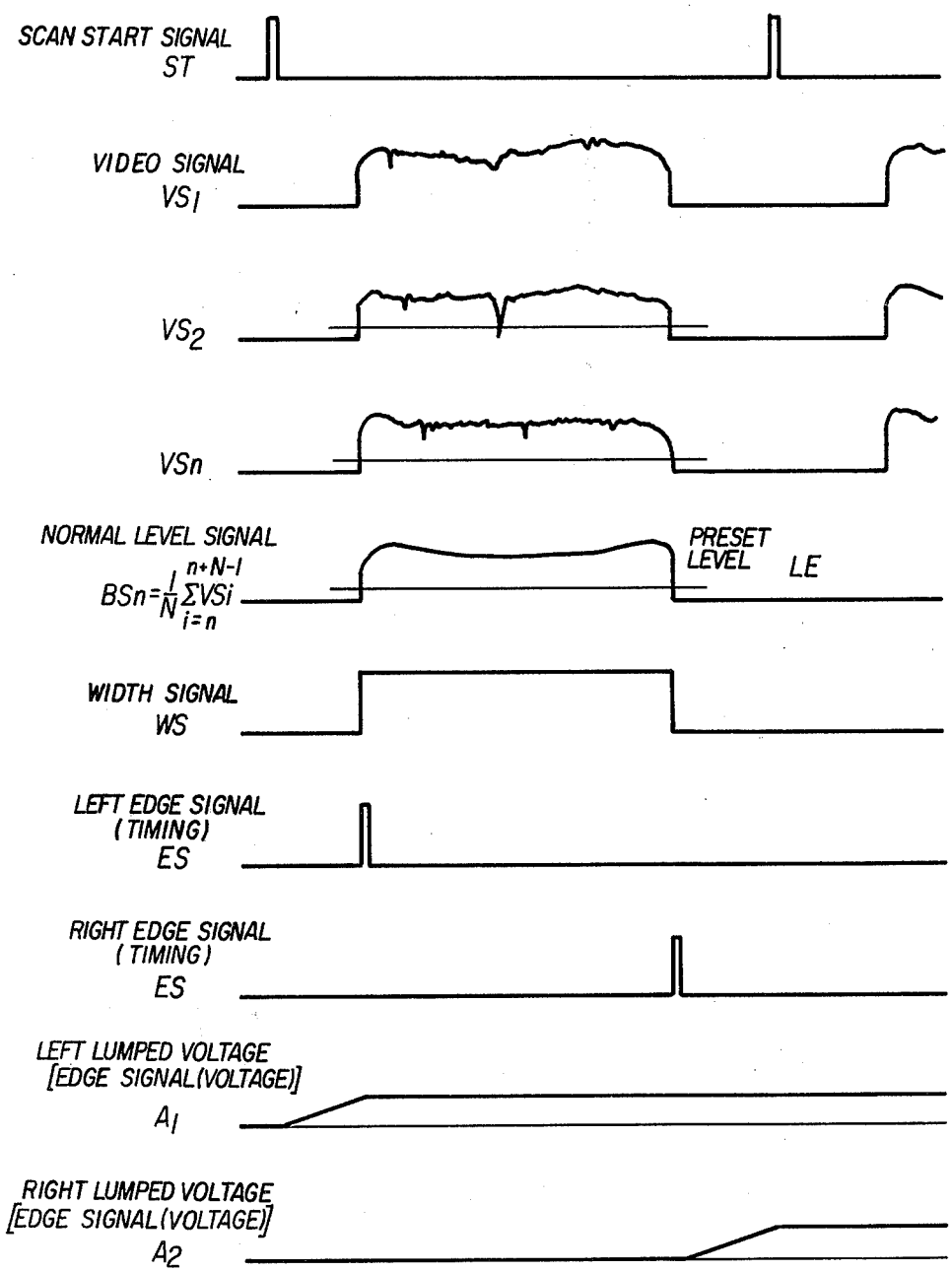
FIG. 39 is an illustration of wave forms appearing at various points of the circuit.

The operation of the signal processor will now be described with reference to the block diagrams of FIGS. 37 and 38 and the wave forms of FIG. 39, assuming that the material 401 has a uniform thickness T. In the same manner as in the signal processing operation described hereinbefore, the video signal produced by the top camera 404 which scans the radiant light image of the top surface of the material 401 is fed through a automatic gain control 413 and converted into an 8-bit (256 steps) digital signal by a high-speed 8-bit A/D converter 414, transmitting the digital signal to a memory 415 acting as a delay line and at the same time to a normal level detector 417. The normal level detector 417 which is the same in construction and operation as the one described hereinbefore, produces a normal level signal BS for the top surface flaw detector 416 which judges the delayed digital signal DDS according to its deviation from the normal level signal BS.

The normal level signal BS which occurs in the course of the signal processing for the flaw detection is used also for edge detection. More particularly, the normal level detector 417 transmits the normal level signal BS to a comparator 421 which compares the signal BS with a certain preset value LE and produces a width signal WS when BS $\geq$ LE. Therefore, the points where BS=LE correspond the opposite edges of the material 401 and the so-called edge signal appears on the positive- and negative- going edges of the width signal WS. In a case where the edges are determined by detecting the levels of the individual video signals VS, a defect which may be on the top surface of the material 402 is often misjudged as an edge since the signal level drop sharply as in the video signal $VS_2$ of FIG. 39. Such misjudgement does not occur in the edge detection based on the normal level signal BS which is free from the influences of surface imperfections.

As the width signal WS is produced by the comparator 421, saw-tooth generators 422A and 422B produce lumped voltages corresponding to the edge positions of the material 402. More particularly, for the left edge, the saw-tooth generator 422A is triggered by the line scan start signal (pulse) ST and the peak value is held by a peak hold circuit 423A before the point in time of the left edge signal (timing pulse) to obtain a lumped voltage $A_1$. For the right edge, the saw-tooth generator 422B is triggered with the right edge signal (timing pulse) and the peak value is held by a peak hold circuit 423B before the point in time of the line scan start signal ST to obtain a lumped voltage $A_2$. The lumped voltages $A_1$ and $A_2$ are voltages corresponding to the left and right edge positions and are fed to the inputs of the servo amplifiers 424A and 424B, respectively, along with the camera position signal voltages $S_1$ and $S_2$ which are fed from the servo motors 411A and 411B or from the potentiometers 412A and 412B which are mounted respectively on the carriages 407A and 407B, thereby to control the positions of the side cameras 405A and 405B through the servo motors 411A and 411B and the carriages 407A and 407B to compensate for positional deviations of the opposite edges of the material 401.

The edge detector 425 is constituted by a comparator 421, saw-tooth generators 422A and 422B, and peak hold circuits 423A and 423B. Indicated at 426A is a signal processor for the left lateral surface and at 426B is a signal processor for the right lateral surface. The reference numeral 440 denotes a timing control circuit.

Figure 40:
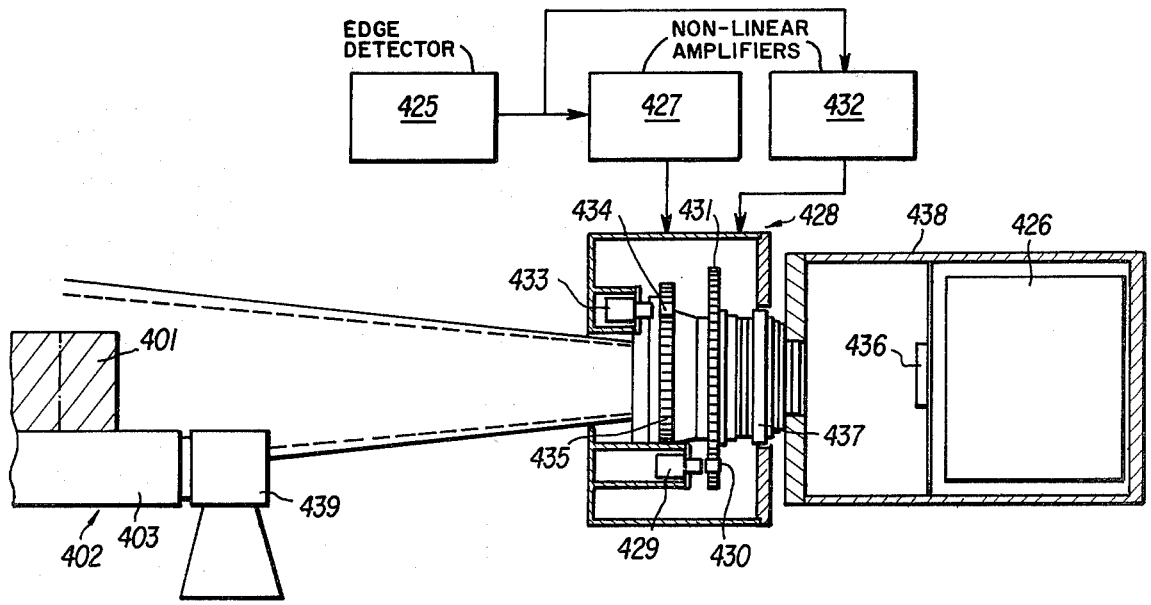
FIG. 40 is a diagrammatic view of an optical follow-up device.

Instead of the mechanical control of the side cameras 405A and 405B, there may be employed an optical control system as shown in FIG. 40. In the optical control system, the edge signal (voltage) produced by an edge detector 425 is fed to a motor drive lens 428 through a non-linear amplifier 427 to actuate a servo motor 429 which rotates a focus adjusting ring 431 about its axis through a gear 430 to focus the motor drive lens 428 on the lateral surface of the material 401. The non-linear amplifier 427 serves to convert the edge signal (voltage) which indicates the position of the lateral surface of the material 401 into a rotational angle (voltage) which is suitable for focusing the motor drive lens 428 on the lateral surface of the material. The edge signal (voltage) actuate the servo motor 433 through a non-linear amplifier 432 to rotate a zoom ring 435 through the zoom adjust gear 434, imaging the material 401 on a sensor 436 at a predetermined magnification. The non-linear amplifier 432 serves to convert the edge signal (voltage) into a rotational angle (voltage) for the zoom ring 435 to have a focal distance of $F = f(L)$ (where F is the focal distance and L is the position of the lateral surface of the material). Therefore, even in a case where the position of the lateral surface is varied between the solid and broken lines due to variations in the width of the material 401 or its meandering movements, the image of the lateral surface is invariably imaged on the censor 436 at constant magnification. Namely, when the material 401 approaches, the field of view is broadened as indicated in solid line, and, when the material 401 moves away, the field of view is narrowed as indicated in broken line in FIG. 40, producing video signals of varying field of view. In FIG. 40, denoted at 437 is a diaphragm adjuster ring, at 438 is a camera box and at 439 is a bearing stand.

Where the thickness T of the conveyed material 401 is constant and its top surface is in a relatively stable state, it is possible to control the side cameras 405A and 405B by the edge signals obtained from the normal level signal BS originating from the video signals of the top camera 404. However, in a case where the thickness T is not constant, the signals from the lower cameras 408A and 408B are used for the control. This is because the material which is conveyed over the rollers 403 has its bottom surface restricted on the level of the rollers 403 in spite of the variations in the thickness T. In such a case, the detection of the edges of the material 401 is more facilitated if the side camera 405B is controlled by the lower camera 408A and the side camera 405A is controlled by the lower camera 408B.

If the variations in the thickness T are very large and there is a possibility of the top surface of the material 401 falling out of the depth of field of the top camera 404, the side cameras 405A and 405B may be used to control the top camera 404 to follow undulations of the top surface.

Thus, in this embodiment, the edges of the conveyed material are detected from the normal level signal which occurs when processing video signals from one camera for the detection of surface imperfections, so that there is no need for providing a sensor or sensors specifically for the follow-up control of another inspecting camera and the edges are detected more economically and reliably without misdetections due to low defect signals.

What is claimed is:

1. A method for detecting imperfections on the surface of a hot radiant material, comprising the steps of:
    obtaining a video signal by electro-optically scanning a radiant light image of said hot material;
    feeding said video signal to a delay means for delaying said video signal for a predetermined time interval and simultaneously feeding said video signal to a peak hold circuit means for holding peak values of said video signal derived by dividing said video signal in a scanning direction into a plurality of picture elements by a plurality of picture splitting pulses;
    obtaining for each picture element a normal level signal sequentially by averaging peak values of a number of picture elements in adjoining areas;
    comparing said peak values of said video signal obtained by passing said video signal through said peak hold circuit means with a current normal level signal obtained in a previous operation;
    slide-averaging fractional signals of said peak values of said video signal wherein each of said fractional signals having a difference from said current normal level signal in excess of a preset value is eliminated and replaced by a previously obtained fractional signal in said slide-averaging process; and
    comparing the delayed video signal from said delay means with said normal level signal to discriminate a surface imperfection according to the difference between said delayed video signal and said normal level signal.

2. A method as set forth in claim 1, wherein said method further comprises the steps of:
    longitudinally and transversely dividing the surface of said material into a plurality of picture elements and collecting particular picture element data by comparing the peak value of said video signal for each picture element with a normal level signal;

preliminarily analysing said surface by shifting sequentially from one picture element to another a small area covering a predetermined number of picture elements in rows and columns while comparing in each shifted position a number of said picture element data in said small area with a total number of picture elements thereof; and analysing said surface by shifting sequentially from one picture element to another a large area covering a predetermined number of picture elements in rows and columns while comparing in each shifted position a number of said picture element data in said large area with a total number of picture elements thereof.

3. A method as set forth in claim 1, wherein said method further comprises the steps of:

extracting subsiding portions of said video signal which fall beneath a preset normal level Po;

calculating the depth P and width W of each of said subsiding signal portions;

obtaining a discriminant function f(P,W) by substituting said depth P and width W into a discriminant equation $$f(P,W) = \frac{W}{\alpha + [\beta (P - Po]^\gamma}$$

wherein said parameters $\alpha$, $\beta$ and $\gamma$ of said discriminant equation are experimentally determined by analysing video signals of at least one similar hot material, plotting various combinations of depth P and width W obtained from said video signals of said at least one hot material on a data map, and curve fitting said discriminant equation to said various values of depth P and width W plotted on said data map;

forming a judgement of "defect" when said discriminant function f(P,W) in one of equal to and greater than a preset value, and forming a negative judgement when said discriminant function f(P,W) is less than said preset value.

4. A surface inspection system for simultaneously inspecting by a plurality of line scan cameras the top, bottom and side surfaces of a hot radial material which is transported along a predetermined transfer passage, said line scan cameras being positioned to scan along lines of intersection where said top, bottom, and side surfaces are intersected by a plane which is disposed perpendicular to the travel direction of said material, comprising:

a top line scan camera positioned above said transfer passage to scan in said plane a line of intersection on said top surface;

a pair of side line scan cameras positioned above said transfer passage and on the outer side of said top line scan camera to scan in said plane the opposite end portions of said line of intersection on said top surface and lines of intersections on opposite side surfaces of said material, said side line scan cameras having a focusing depth of field greater than the thickness of said material, said side line scan cameras being directed along a first pair of optical axes which form acute angles with respect to the top surface of said material; and a pair of lower line scan cameras positioned beneath and on the opposite sides of said transfer passage to scan obliquely from beneath a line of intersection on the bottom surface of said material in a plane containing said line of intersection on the bottom surface and slanted downward in the direction of travel of said material, said lower line scan cameras being directed along a second pair of optical axes which form acute angles with respect to the bottom surface of said material.

5. A camera follow-up control device for a surface inspection system of the type which employs more than one camera for simultaneously viewing different surfaces of a hot radiant material in travel over a transfer passage and which is provided with means for processing video signals into normal level signals thereby to discriminate imperfections on said surfaces, said follow-up control device comprising:

means for detecting edge signals by comparing the normal level signal of one of two adjacent surfaces with a preset value; and means for controlling follow-up movements of a camera for the other one of said two adjacent surfaces in accordance with said edge signals.

* * * * *

UNITED STATES PATENT AND TRADEMARK OFFICE
CERTIFICATE OF CORRECTION

PATENT NO. : 4,319,270

DATED : March 9, 1982

INVENTOR(S) : NOBUO KIMURA ET AL

It is certified that error appears in the above—identified patent and that said Letters Patent is hereby corrected as shown below:

Figure 11, added in accordance with the attached drawing.

Signed and Sealed this

Fourteenth Day of September 1982

[SEAL]

Attest:

*Attesting Officer*

GERALD J. MOSSINGHOFF

*Commissioner of Patents and Trademarks*

UNITED STATES PATENT AND TRADEMARK OFFICE
CERTIFICATE OF CORRECTION

PATENT NO. : 4,319,270

DATED : March 9, 1982

INVENTOR(S) : NOBUO KIMURA ET AL

It is certified that error appears in the above—identified patent and that said Letters Patent is hereby corrected as shown below:

On the title page
In the Abstract, line 3, change "for" to --of--.
Column 1, line 36, change "deflects" to --defects--.
Column 3, line 32, change "scale" to --scales--.
Column 6, line 47, change "dinamic" to --dynamic--.
Column 11, line 3, change "signls" to --signals--.
Column 13, line 59, change "storage" (first occurrence) to --stored--.
Column 14, line 25, change "degree of defectiveness and with" to --degree of defectiveness along with--; line 27, change "degree" to --degrees--; delete "with" and substitute --including--; delete "of" and substitute --due to--.
Column 15, line 60, delete "P." and substitute --P,--.
Column 18, line 42, change "a" to --an--.
Column 18, line 60, after "correspond" insert --with--.
Column 19, line 49, change "actuate" to --actuates--.
Column 21, line 26, after "Po" in the equation, insert --)--.
Column 21, line 44, change "radial" to --radiant--.

Signed and Sealed this

Fifteenth Day of February 1983

[SEAL]

Attest:

GERALD J. MOSSINGHOFF

Attesting Officer

Commissioner of Patents and Trademarks